US008036757B2

(12) United States Patent
Worley

(10) Patent No.: US 8,036,757 B2
(45) Date of Patent: Oct. 11, 2011

(54) PACING LEAD AND METHOD FOR PACING IN THE PERICARDIAL SPACE

(76) Inventor: Seth Worley, Lancaster, PA (US)

( * ) Notice: Subject to any disclaimer, the term of this patent is extended or adjusted under 35 U.S.C. 154(b) by 757 days.

(21) Appl. No.: 11/535,374

(22) Filed: Sep. 26, 2006

(65) Prior Publication Data
US 2008/0065185 A1     Mar. 13, 2008

Related U.S. Application Data

(60) Provisional application No. 60/825,139, filed on Sep. 10, 2006.

(51) Int. Cl.
*A61N 1/375* (2006.01)
(52) U.S. Cl. ......... 607/127; 607/122; 607/126; 607/129
(58) Field of Classification Search .................. 607/122, 607/126, 127, 128, 129
See application file for complete search history.

(56) References Cited

U.S. PATENT DOCUMENTS

| | | | |
|---|---|---|---|
| 4,481,953 A * | 11/1984 | Gold et al. ................... | 607/122 |
| 4,497,326 A | 2/1985 | Curry | |
| 4,628,943 A | 12/1986 | Miller | |
| 4,667,686 A | 5/1987 | Peers-Travarton | |
| H356 H | 11/1987 | Stokes et al. | |
| 4,865,037 A | 9/1989 | Chin et al. | |
| 4,886,074 A | 12/1989 | Bisping | |
| 4,953,564 A | 9/1990 | Berthelsen | |
| 5,020,545 A | 6/1991 | Soukup | |
| 5,033,477 A | 7/1991 | Chin et al. | |
| 5,152,299 A | 10/1992 | Soukup | |
| 5,259,395 A | 11/1993 | Li | |
| 5,336,252 A | 8/1994 | Cohen | |
| 5,383,924 A | 1/1995 | Brehier | |
| 5,425,756 A | 6/1995 | Heil, Jr. et al. | |
| 5,507,743 A | 4/1996 | Edwards et al. | |
| 5,514,174 A | 5/1996 | Heil, Jr. et al. | |
| 5,683,447 A * | 11/1997 | Bush et al. ................... | 607/126 |
| 5,830,222 A | 11/1998 | Makower | |
| 5,837,006 A | 11/1998 | Ocel et al. | |
| 5,968,010 A | 10/1999 | Waxman et al. | |
| 6,010,526 A | 1/2000 | Sandstrom et al. | |
| 6,068,638 A | 5/2000 | Makower | |
| 6,071,279 A * | 6/2000 | Whayne et al. ............... | 607/122 |
| 6,071,292 A | 6/2000 | Makower et al. | |
| 6,190,353 B1 | 2/2001 | Makower et al. | |
| 6,200,303 B1 | 3/2001 | Verrior et al. | |

(Continued)

OTHER PUBLICATIONS

PCT International Search Report, Mar. 13, 2008, Worley.

*Primary Examiner* — Scott Getzow
*Assistant Examiner* — Joseph Dietrich
(74) *Attorney, Agent, or Firm* — Patterson Thuente Christensen Pedersen, P.A.

(57) ABSTRACT

A pacing lead for implantation in the pericardial space includes an elongated lead body, a compression fixation element, and at least one electrode on either the lead body or the fixation element. The fixation element defines a resilient structure, and is positioned and dimensioned so that when the lead is disposed in the pericardial space, the resilient fixation element is compressed between the parietal and visceral pericardium, thereby biasing the electrode against the myocardium and providing positional stabilization to the lead. Further positional stability may be provided mechanically with structures enabling the application of adhesive or with fixation screw or tine elements.

17 Claims, 16 Drawing Sheets

U.S. PATENT DOCUMENTS

| | | |
|---|---|---|
| 6,356,791 B1 * | 3/2002 | Westlund et al. ............. 607/115 |
| 6,375,615 B1 | 4/2002 | Flaherty et al. |
| 6,490,489 B2 | 12/2002 | Bornzin et al. |
| 6,493,591 B1 * | 12/2002 | Stokes .................. 607/127 |
| 6,535,764 B2 | 3/2003 | Imran et al. |
| 6,554,230 B1 | 4/2003 | Horski |
| 6,591,998 B2 | 7/2003 | Haynes et al. |
| 6,684,109 B1 | 1/2004 | Osypka |
| 6,931,286 B2 | 8/2005 | Sigg et al. |
| 7,103,418 B2 | 9/2006 | Laske et al. |
| 2002/0111619 A1 | 8/2002 | Keast et al. |
| 2002/0165535 A1 | 11/2002 | Lesh et al. |
| 2003/0109809 A1 | 6/2003 | Jen et al. |
| 2003/0212446 A1 | 11/2003 | Kaplan et al. |
| 2004/0015191 A1 | 1/2004 | Otman et al. |
| 2004/0064172 A1 * | 4/2004 | McVenes et al. ............. 607/122 |
| 2005/0197692 A1 | 9/2005 | Pai et al. |
| 2006/0009827 A1 | 1/2006 | Kurth et al. |

* cited by examiner

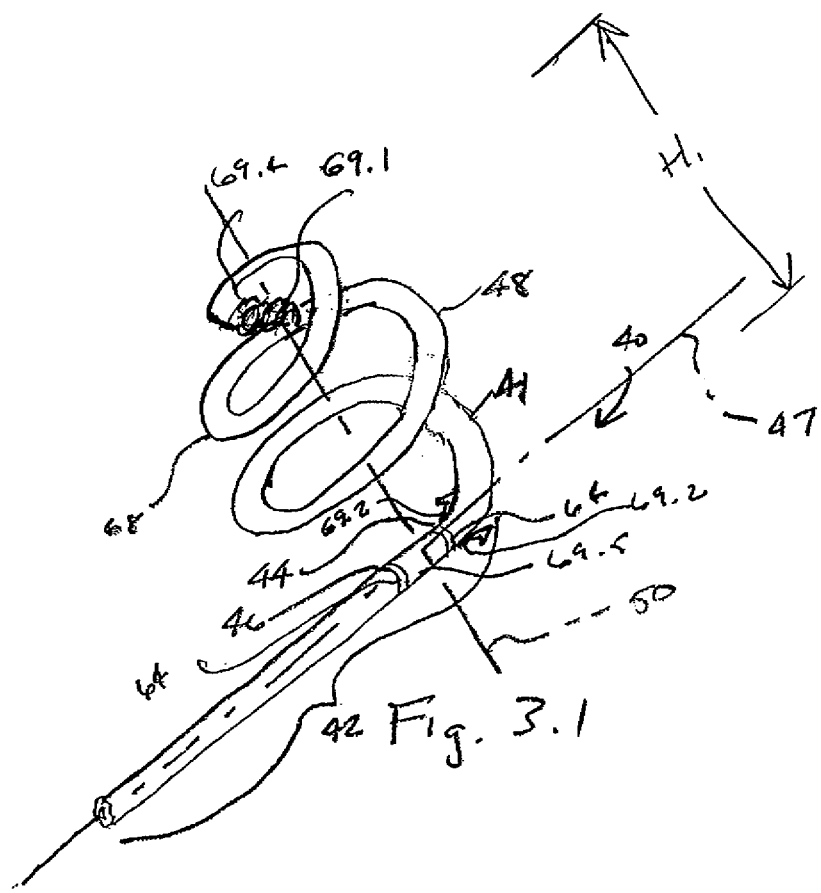
Fig. 3.1
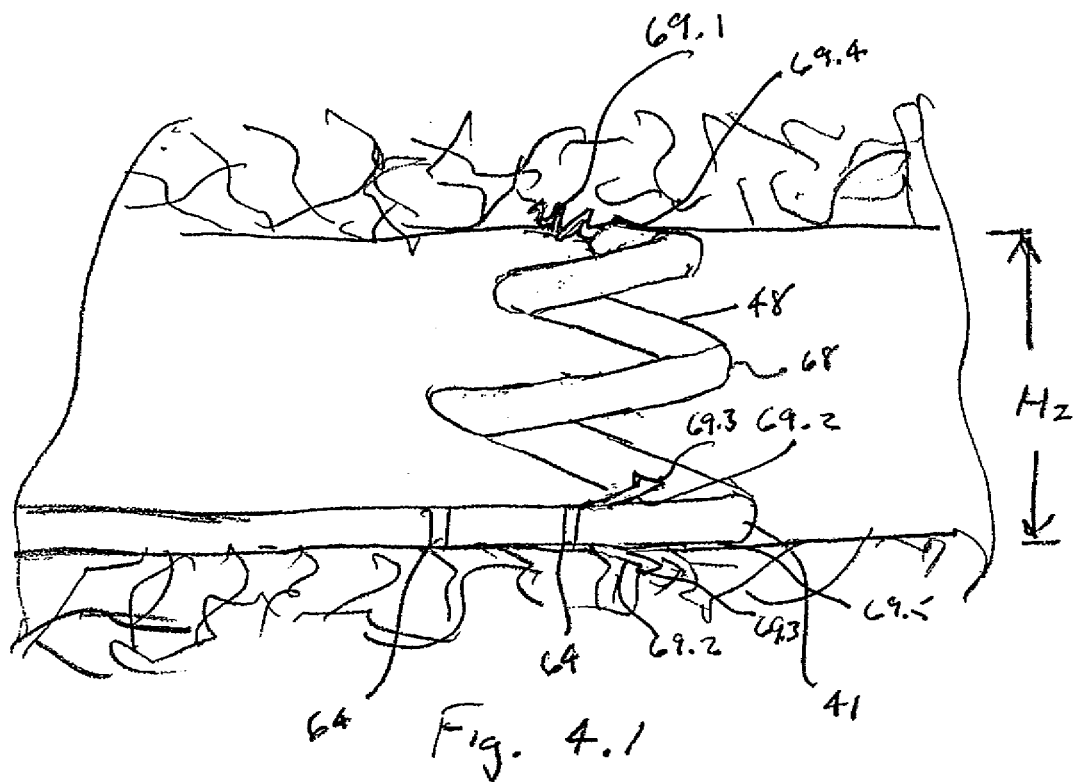
Fig. 4.1

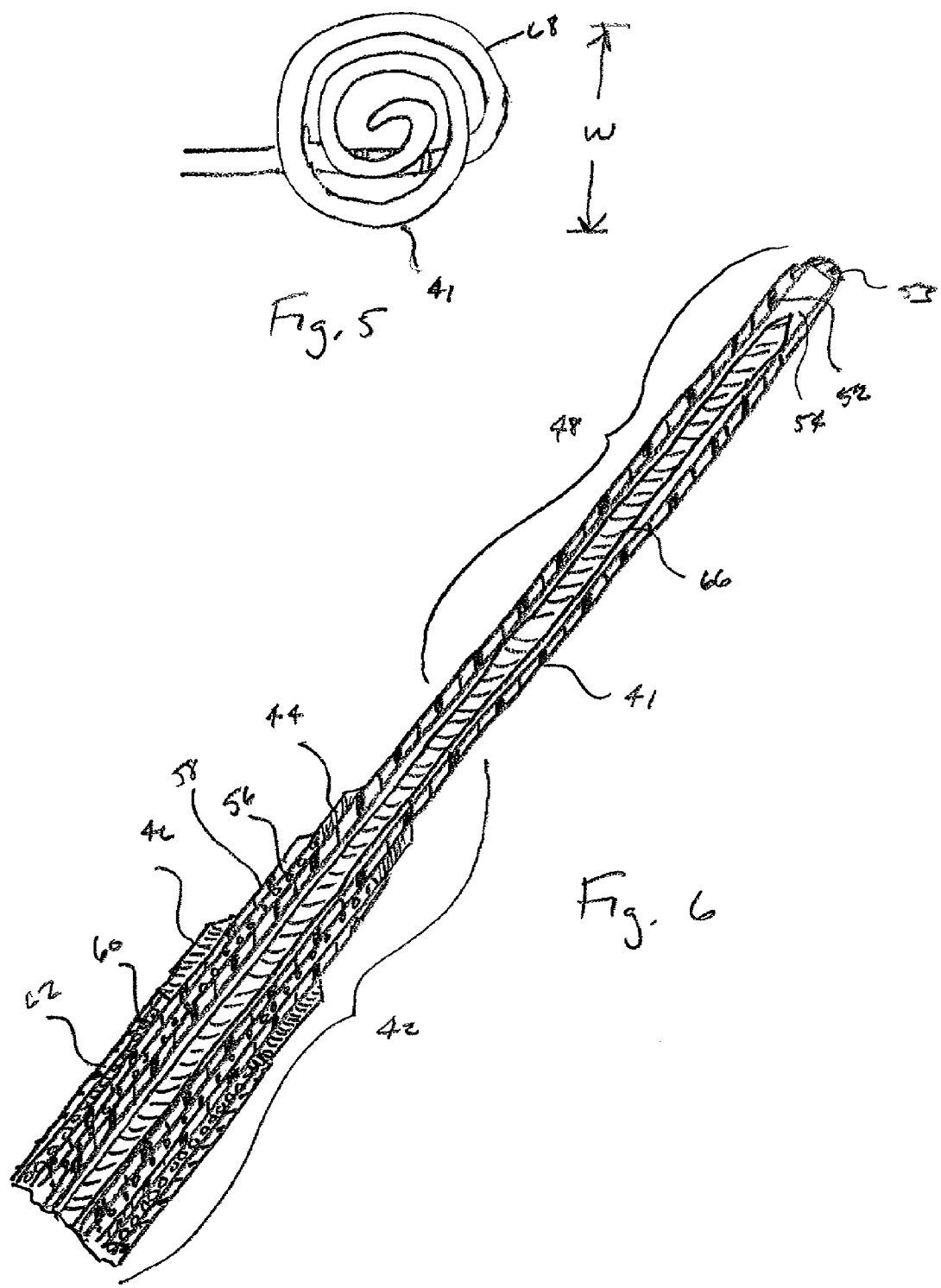

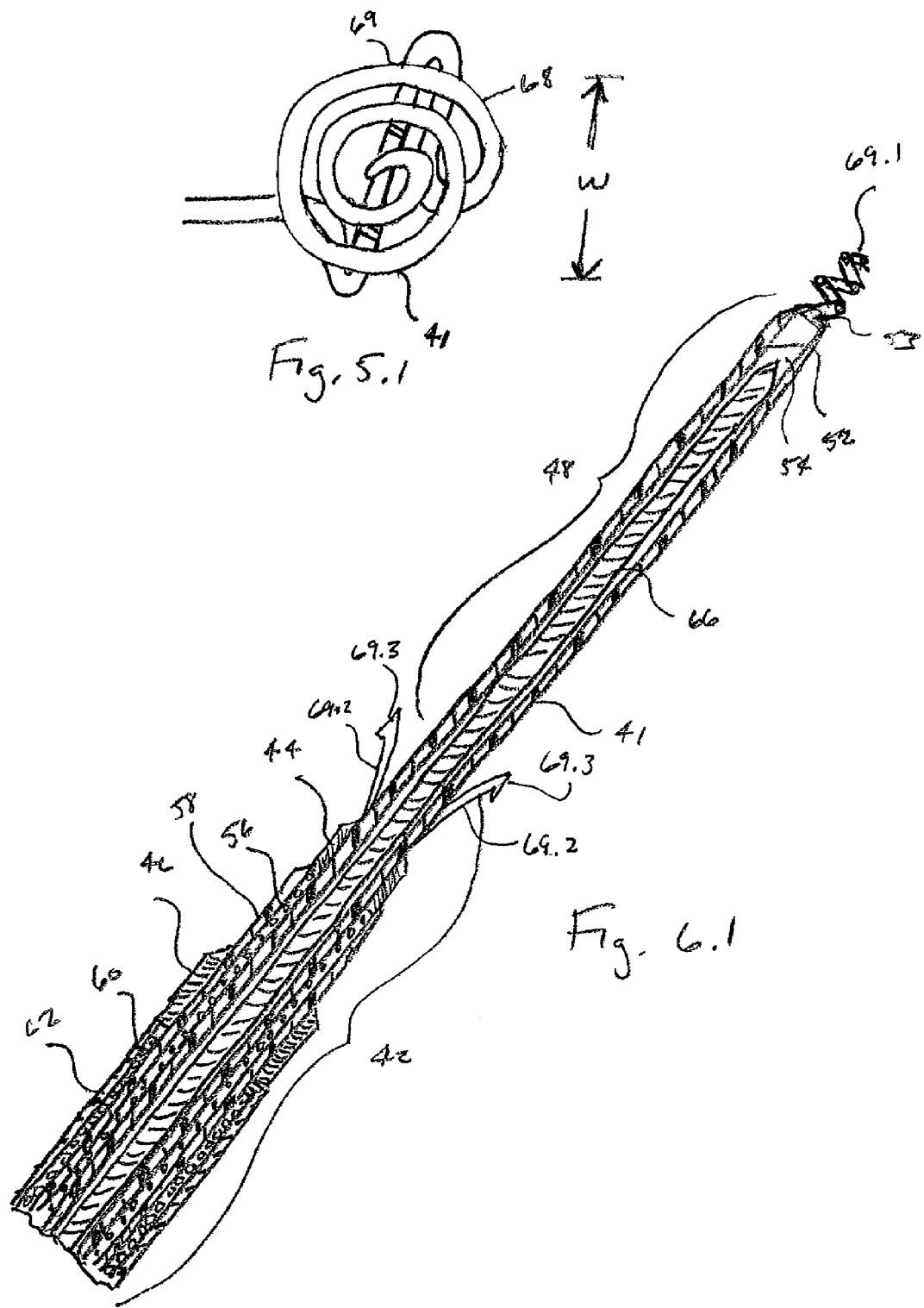

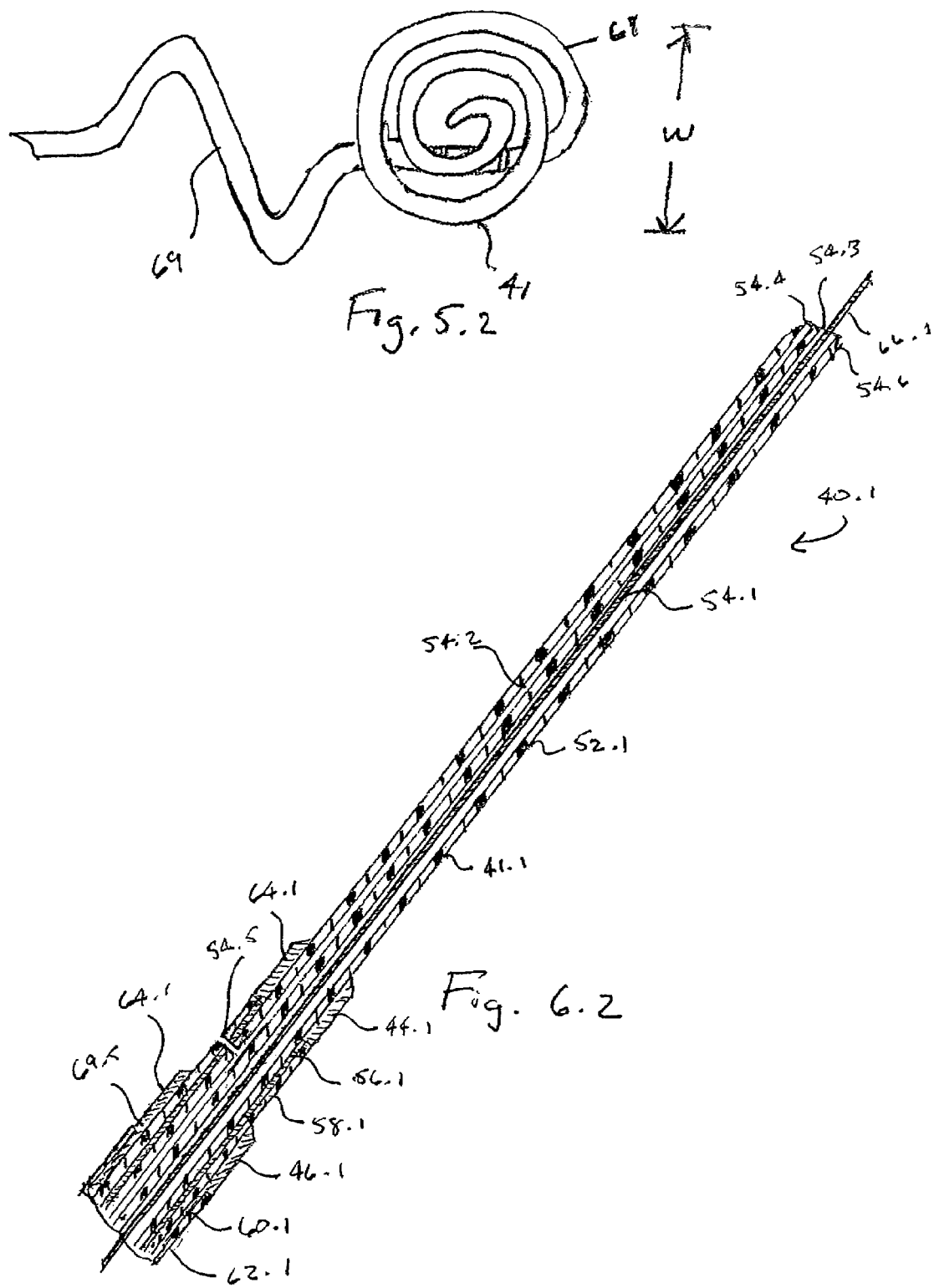

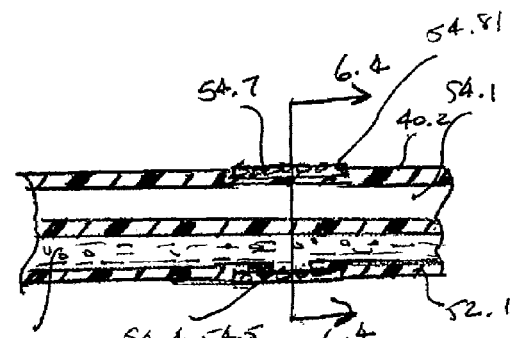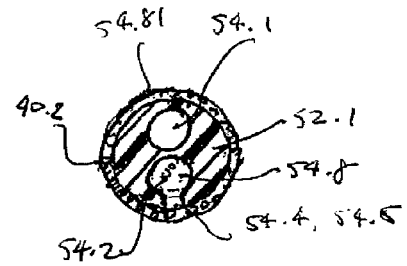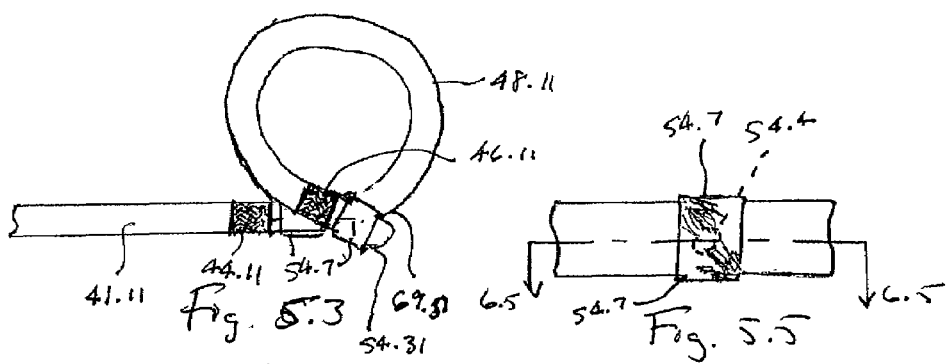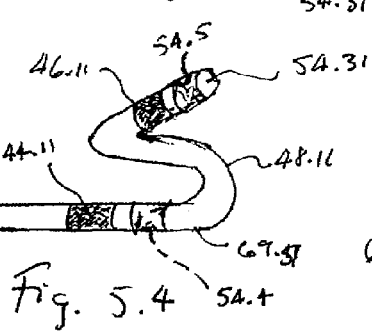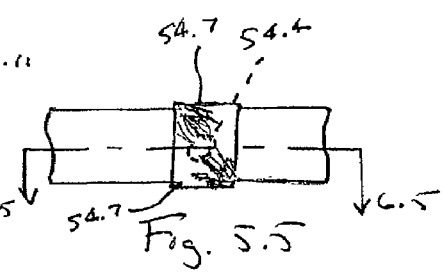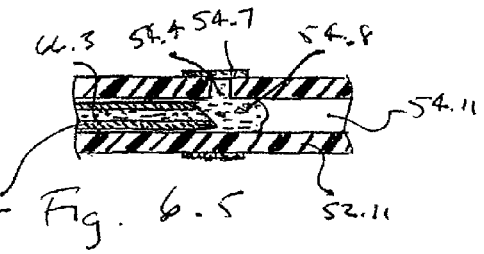

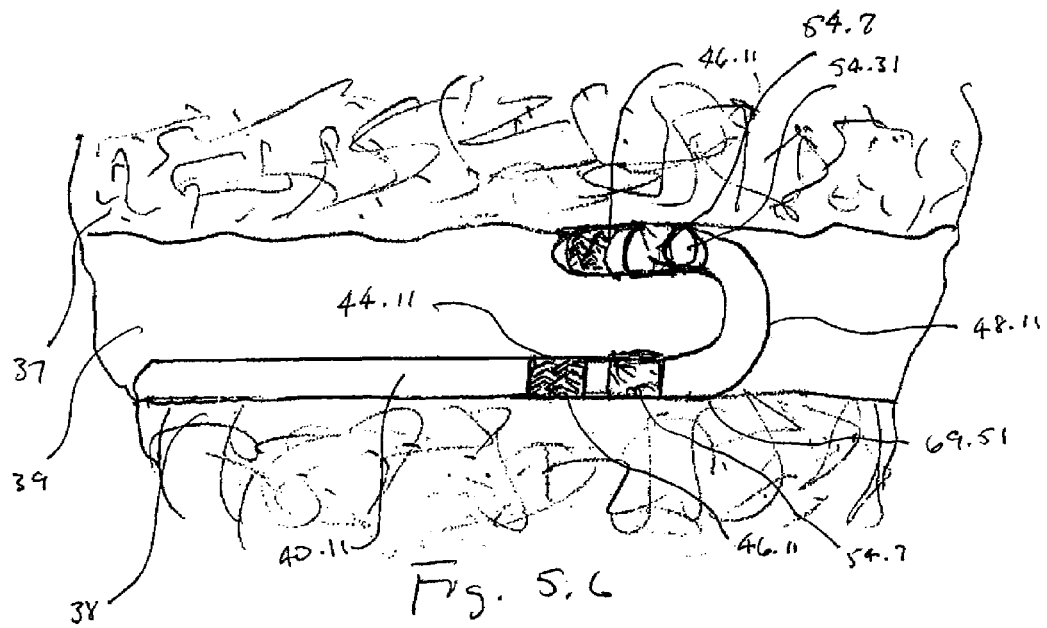
Fig. 5.6
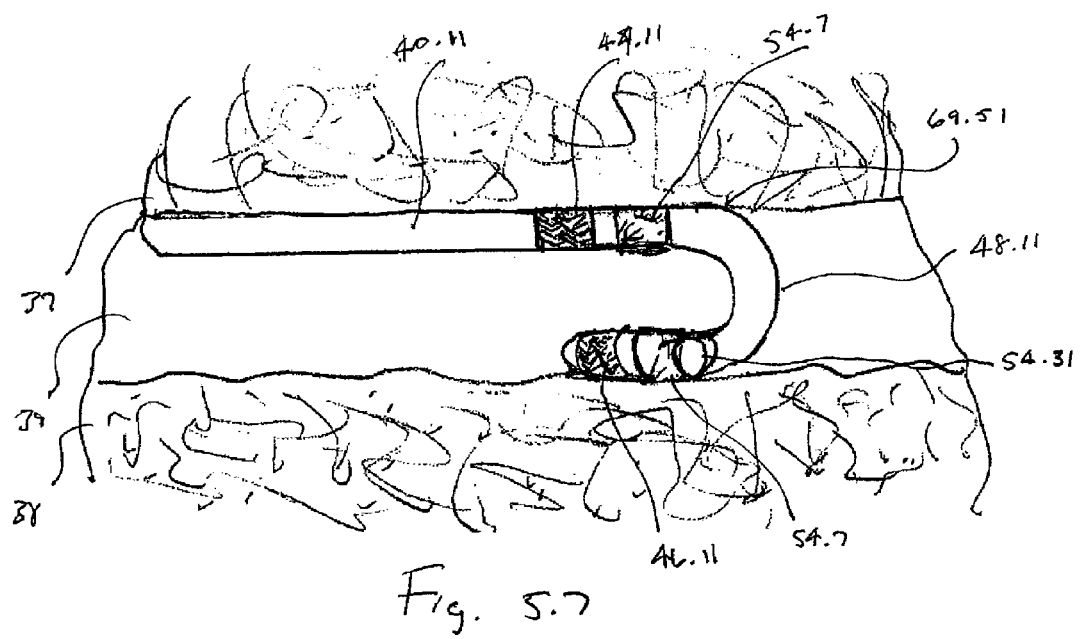
Fig. 5.7

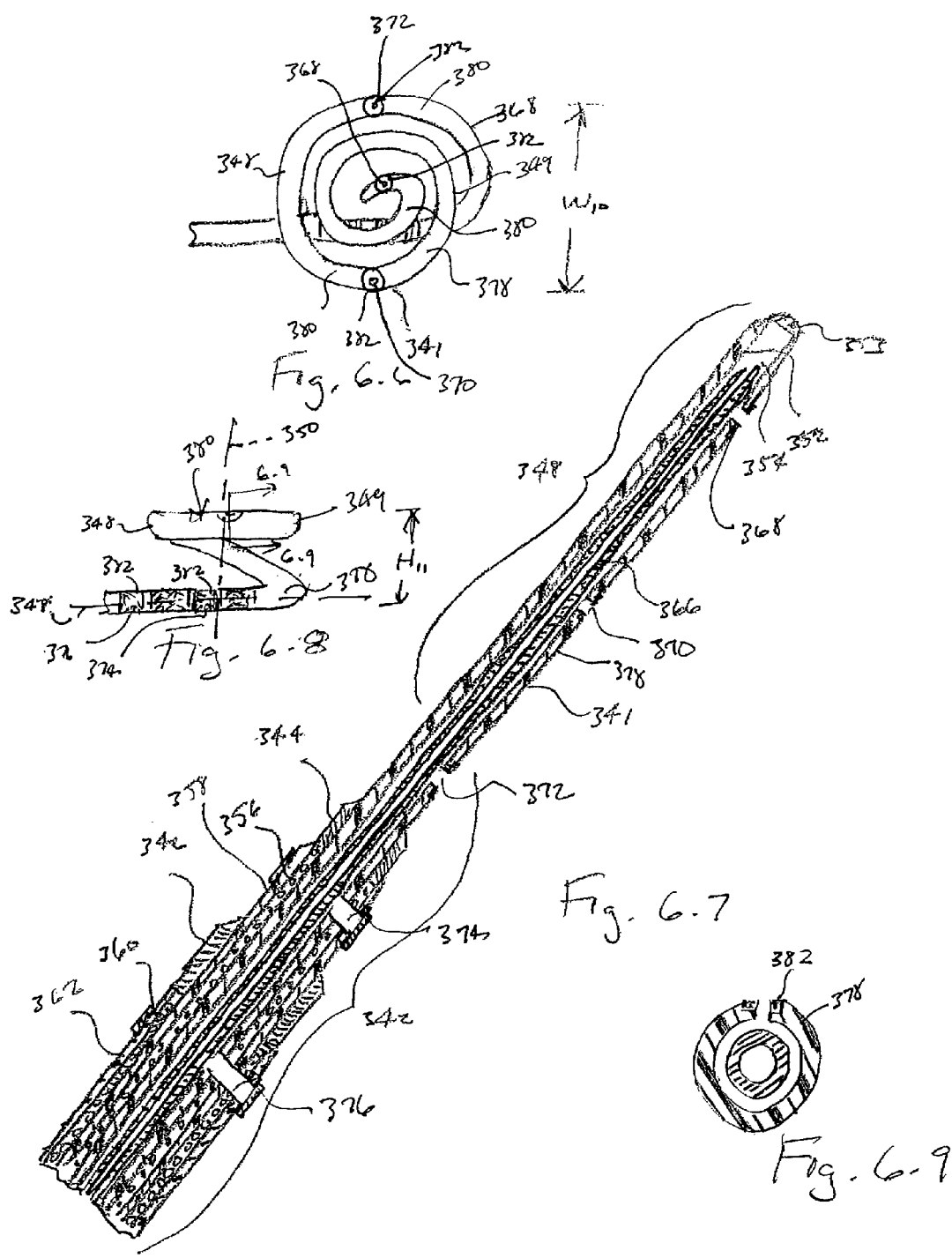

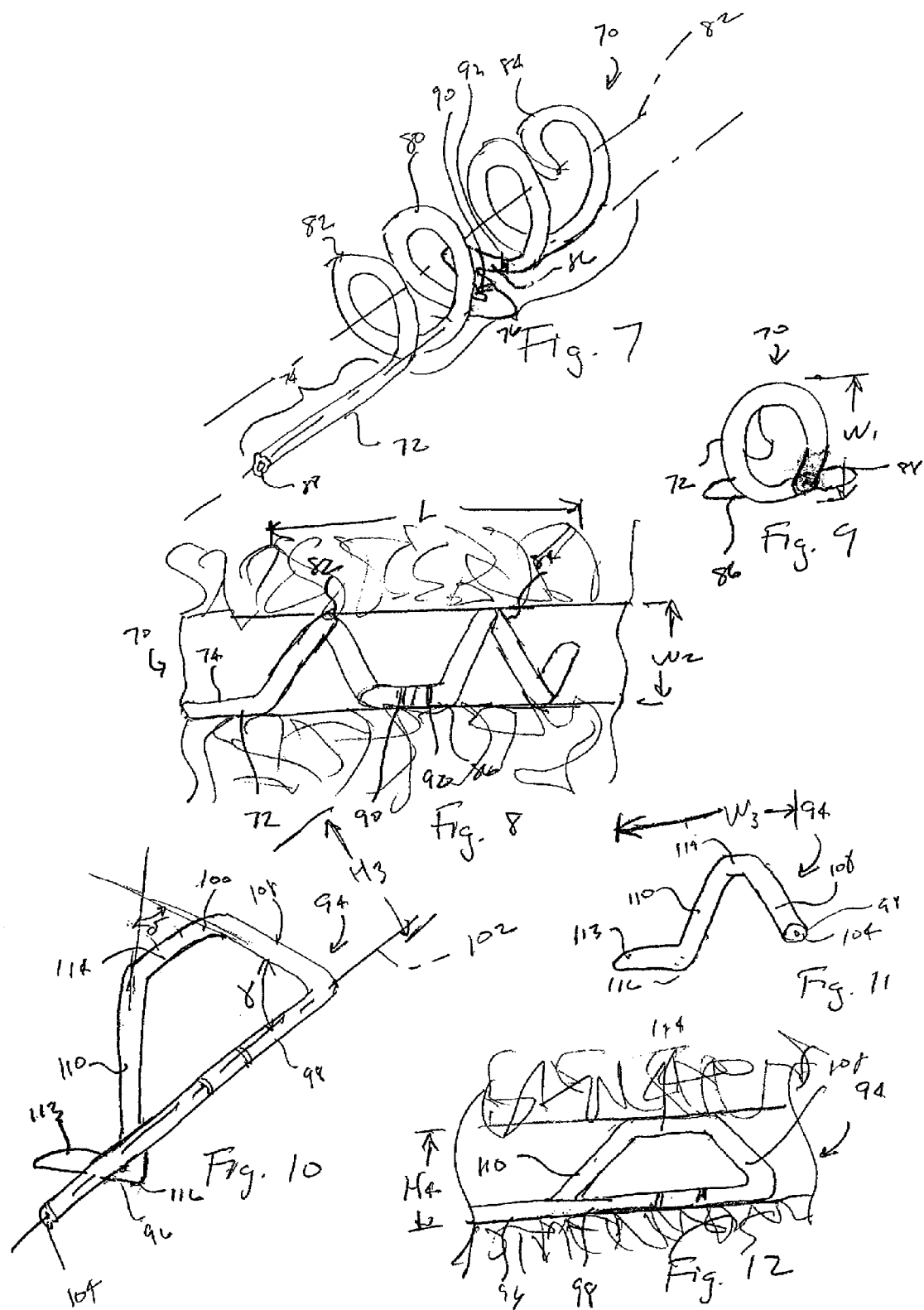

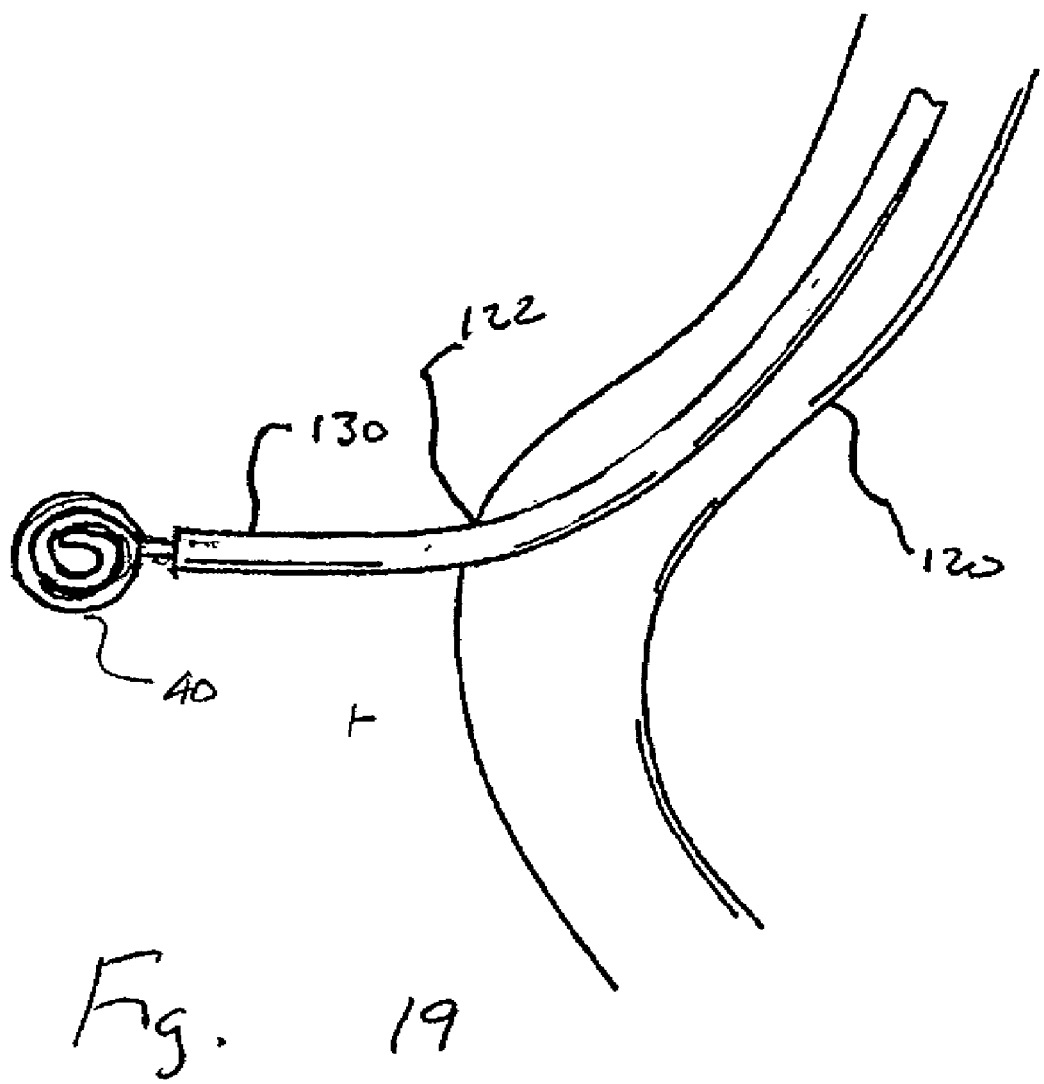

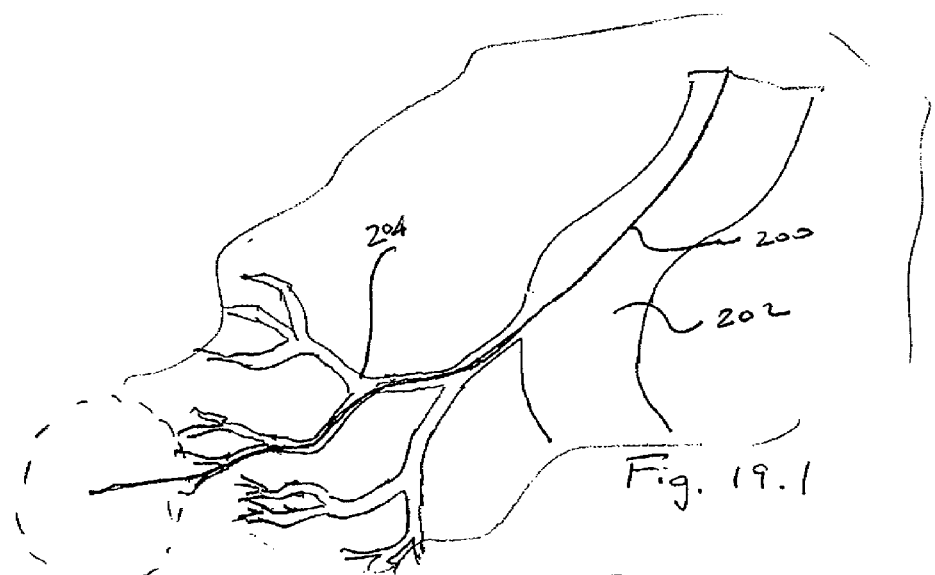
Fig. 19.1
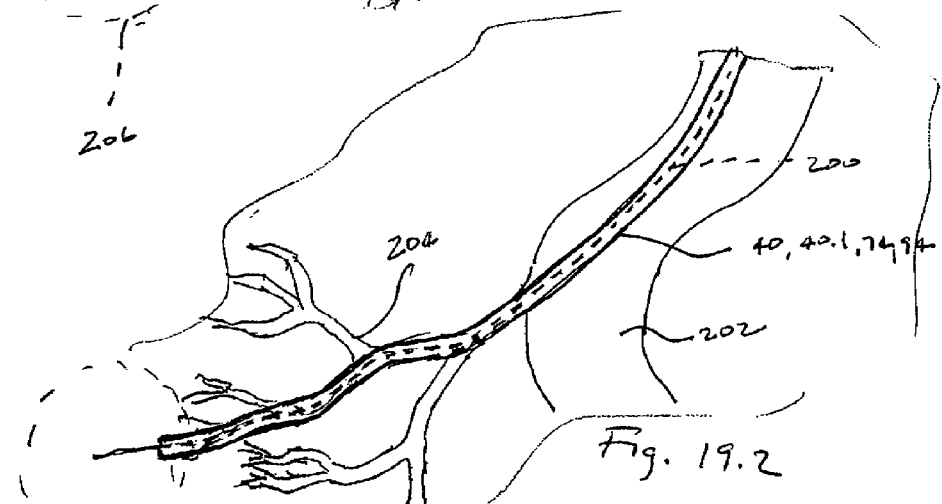
Fig. 19.2
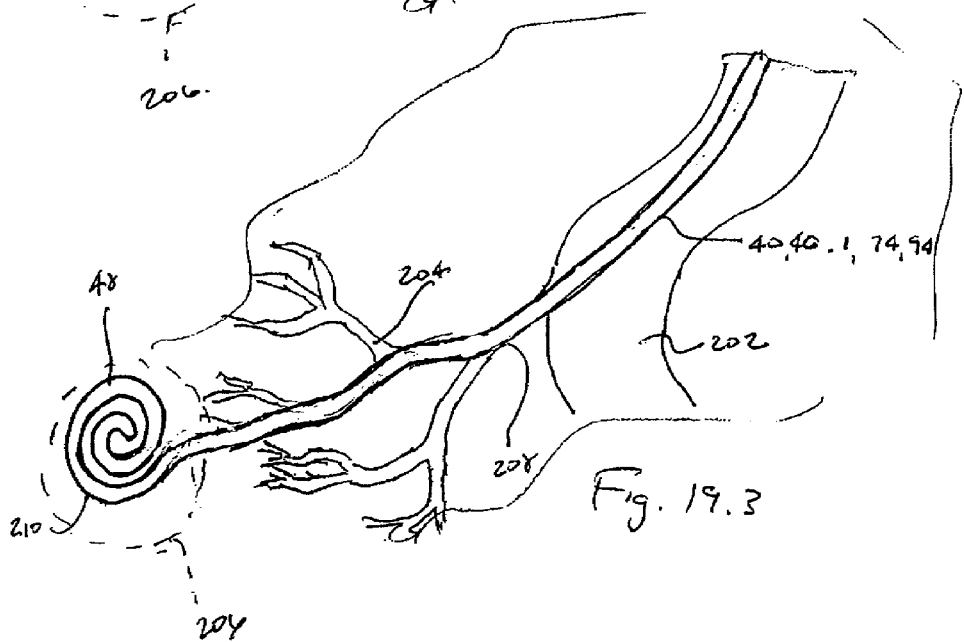
Fig. 19.3

PACING LEAD AND METHOD FOR PACING IN THE PERICARDIAL SPACE

RELATED APPLICATIONS

This application claims the benefit of U.S. Provisional Patent Application No. 60/825,139, entitled PACING LEAD AND METHOD FOR PACING IN THE PARICARDIAL SPACE, filed Sep. 10, 2006, and hereby fully incorporated herein by reference.

FIELD OF THE INVENTION

The present invention relates generally to pacing leads. More particularly, the present invention relates to pacing leads for implantation between the visceral and parietal pericardium of the heart.

BACKGROUND OF THE INVENTION

As depicted in FIGS. 1 and 2, the human heart 30 is contained in the mediastinum 32 within a conical sac of serous membrane called the pericardium 34. There are generally two layers to pericardium 34; the fibrous pericardium 35 and the serous pericardium 36. The fibrous pericardium 35 is a superficial layer comprising dense connective tissue and it encloses serous pericardium 36. The serous pericardium 36 itself has two layers. The layer adjacent the fibrous pericardium is the parietal layer 37 and the layer next to the heart is the visceral layer 38, also known as the epicardium. Between the parietal 37 and visceral 38 layers exists a small cavity known as the pericardial space 39. This pericardial space may be void or partially filled with a lubricious fluid 39a.

Pacing of the heart is usually achieved by pacing leads introduced transvenously. In some cases, however, the chamber of the heart or a specific location on the chamber of the heart is not accessible using a transvenous approach and must be placed surgically.

Leads placed on the surface of the heart, such as in contact with the visceral pericardium, require a method of fixation to keep them in place. In the prior art, pacing the epicardium is usually accomplished via a screw in lead placed surgically.

To pace the epicardium, a pacing lead is positioned with one or more electrodes in contact with the visceral pericardium. For effective pacing, electrodes on the pacing lead must be in constant electrical conductive contact with the surface of the visceral pericardium. Conductivity is most preferably sufficient so as to enable a pacing voltage of 3 volts or less, although for various reasons, prior art leads often develop much higher pacing thresholds.

To accomplish constant contact, different pacing lead configurations have been previously used to assist in the placement and retention of the pacing lead in the desired position. These prior leads, however, all have certain drawbacks making them not entirely satisfactory. For example they require placement through the parietal pericardium either surgically or percutaneously. They are usually screwed into place and frequently develop high thresholds. Other leads have been developed which employ a helical structure oriented along the longitudinal axis of the lead. The helical structure exerts a lateral biasing force against the walls of the space to assist in fixation of the lead. These prior helical leads, however, are sometimes difficult to stabilize and may be prone to "overturn" or rotate about the longitudinal axis of the lead when in place, thereby interrupting electrical contact of the electrodes.

The present inventor has recognized that prior art leads and fixation methods that do not employ screws or suture are not entirely suitable for placement in the pericardial space through the pericardium (surgical or percutaneously). Further, the present inventor recognizes that prior art leads, fixation and stabilization methods are not entirely suitable for leads introduced into the pericardial space through the venous system. Hence, there is still a need for a lead and passive fixation method assuring stable pacing from the epicardial surface whether introduced transvenously through the coronary venous microcirculation or through the wall of a chamber of the heart or through the fibrous pericardium. Because the general problems discussed above have not been addressed by conventional pacing leads, there is a current need for pacing leads addressing the problems and deficiencies inherent with the prior designs.

SUMMARY OF THE INVENTION

The pacing lead of the various embodiments of the present invention substantially addresses the aforementioned problems of conventional designs by providing lead shapes, methods of fixation, and methods of pacing lead deployment that assure that the electrodes of the lead are firmly in electrical conductive contact with the epicardial surface and the lead is positionally stable. The lead of the present invention may thereby enable relatively low pacing voltages, generally 3 volts or less. In an embodiment, the improved stability and pacing is accomplished when a resilient fixation structure in the form of a helix, loop, or other resilient structure is compressed between the parietal and visceral pericardium when disposed in the pericardial space. The biasing force exerted by compression of the helical fixation element biases electrodes on the lead body against the visceral pericardium thereby improving electrical conductivity between the myocardium and the electrodes, and providing a degree of positional stability. Positional stability of the lead may be further enhanced in some embodiments with bio-compatible adhesive introduced at desired locations to adhere the lead body to surrounding tissues.

In an embodiment, the lead has a proximal portion and a distal portion comprising a resilient fixation element extending from the proximal portion. The proximal portion includes a pair of electrodes. The compression fixation element may be preformed in a helix or other shape enabling resiliency. The height or width dimension of the fixation element is predetermined so as to be larger than space between the visceral and parietal pericardium. When the lead is advanced into the pericardial space, the fixation element is compressed by the walls of the heart defining the pericardial space, specifically the visceral pericardium and the myocardium. The electrodes of the pacing portion, which may be disposed proximate the fixation element, are biased against the myocardium by the resilience of the fixation element. Electrical conductivity between the electrodes and the myocardium is thereby improved, along with lead stability and pacing and sensing thresholds.

According to an embodiment, a pacing lead for implantation in the pericardial space typically includes a fixation element extending from the pacing portion and defining a generally helical shaped fixation structure extending generally perpendicular to the pacing portion. The helical structure presents a predetermined vertical dimension greater than the dimension of the space between the visceral and parietal pericardium. When the helical structure is advanced into the pericardial space, the helical structure is laterally compressed by the parietal pericardium and at least one electrode is biased against the myocardium According to an embodiment of a method according to the invention, a pacing lead is provided having a lead body with a resilient fixation element extending therefrom. The resilient fixation element is preformed in a helical or loop configuration or other configuration as required to provide positional stability and electrode contact within the pericardial space.

According to the method, the expanded form of the fixation element is deployed by removing a guide wire or stylet slidably disposed in a lumen defined centrally or asymmetrically in the lead. The fixation element, being compressed by the visceral and parietal pericardium, biases electrodes on the lead body or fixation element against the myocardium A feature and advantage of an embodiment of the invention is that any chamber of the heart can be paced by positioning the electrodes on the epicardial surface.

A feature and advantage of an embodiment of the invention is that assuring constant contact between the lead electrodes and myocardium via compression fixation can increase the stability of the fixation and pacing.

A feature and advantage of an embodiment of the invention is that the design of the pacing lead enables use on various sized leads without sacrificing stability or pacing/sensing thresholds A feature and advantage of an embodiment of the invention is a method of pacing lead deployment assuring constant contact between the lead electrodes and the myocardium.

A feature and advantage of an embodiment of the invention is that the heart can be paced by biasing one or more lead electrode against the myocardium using the resilient fixation element of the lead.

A feature and advantage of an embodiment of the invention is that positional stability of the electrodes may be enhanced by the application of adhesive in desired locations to adhere the lead to surrounding tissues.

A feature and advantage of embodiment of the invention is that a lead may be introduced transvenously into the heart and from there into the pericardial space through the coronary venous structure or directly though the wall of one of the chambers such as the right atrial appendage or right atrium. By using the coronary venous microcirculation as a means to access the pericardial space, the final position of the lead and the site where the lead exits the vein into the pericardial space can be kept in close proximity. By comparison, standard leads that stay within the vein can only be placed where there are veins large enough to accommodate the body of the lead. With a lead according to the invention, small veins may be used to position the guide wire where the lead is to be positioned, and the lead may then be advanced along the wire to the desired site by dilating the small veins to the point of rupture at which point the tip of the lead is not within the vein and the tip may be stabilized to ensure electrode contact.

A feature and advantage of an embodiment of the invention is that when advanced into the pericardial space though the venous microcirculation, the proximal portion of the lead will be stabilized and supported within the venous system.

A feature and advantage of an embodiment of the invention is that the pacing lead may be introduced transvenously into the heart and from there into the pericardial space through a coronary venous structure or directly through the wall of one of the chambers such as the right atrial appendage or right atrium.

A feature and advantage of an embodiment of the invention is that the resilient fixation element of the lead may or may not contain electrodes for sensing and pacing the myocardium via the pericardial space.

BRIEF DESCRIPTION OF THE DRAWINGS

FIG. 3.1 is a perspective view of an alternative embodiment of the lead depicted in FIG. 3;

FIG. 5 is a top view of the pacing lead depicted in FIG. 3;

FIG. 5.1 is a top view of an alternative embodiment of the lead depicted in FIG. 3;

FIG. 5.2 is a top view of another alternative embodiment of the lead depicted in FIG. 3;

FIG. 5.3 is a top view of another alternative embodiment of a pacing lead according to the present invention;

FIG. 5.4 is a side view of the lead depicted in FIG. 5.3;

FIG. 5.5 is a fragmentary side elevation of an adhesive port of a lead according to an embodiment of the present invention;

FIG. 5.6 is a side view of the pacing lead depicted in FIG. 5.3 deployed upright in the pericardial space;

FIG. 5.7 is a side view of the pacing lead depicted in FIG. 5.3 deployed inverted in the pericardial space;

FIG. 6 is a longitudinal cross-sectional view of the pacing lead depicted in FIG. 3, straightened with a stylet disposed in a lumen of the lead;

FIG. 6.1 is a longitudinal cross-sectional view of an alternative embodiment of the pacing lead depicted in FIG. 3, straightened with a stylet disposed in a lumen of the lead;

FIG. 6.2 is a longitudinal cross-sectional view of another alternative embodiment of the pacing lead depicted in FIG. 3, straightened with a guidewire disposed in a lumen of the lead;

FIG. 6.3 is a fragmentary longitudinal cross-sectional view of an adhesive port in a lead according to an embodiment of the invention;

FIG. 6.4 is a transverse cross-sectional view of the lead of FIG. 6.3 taken at section 6.4-6.4;

FIG. 6.5 is a cross-sectional view of the lead of FIG. 5.5 taken at section 6.5-6.5;

FIG. 6.6 is a top view of another alternative embodiment of a pacing lead according to the present invention;

FIG. 6.7 is a longitudinal cross-section of the lead depicted in FIG. 6.6;

FIG. 6.8 is a side elevation view of the lead depicted in FIG. 6.6;

FIG. 6.9 is a transverse cross-sectional view of the lead of FIG. 6.8 taken at section 6.9-6.9;

FIG. 7 is a perspective view depicting an alternative embodiment of the pacing lead for the pericardial space according to the present invention;

FIG. 8 is a side view of the pacing lead depicted in FIG. 7 deployed in the pericardial space, FIG. 9 is an end view of the pacing lead depicted in FIG. 7;

FIG. 10 is a perspective view depicting another alternative embodiment of the pacing lead for the pericardial space according to the present invention;

FIG. 11 is a side view of the pacing lead depicted in FIG. 10 deployed in the pericardial space, FIG. 12 is an end view of the pacing lead depicted in FIG. 10;

FIG. 19 is a simplified diagrammatic side cross section view of the region of FIG. 15 depicting the pacemaker lead in the microvasculature or pericardial space having assumed a preformed shape after a stiffening stylet or wire has been withdrawn;

FIG. 19.1 is a simplified diagrammatic view of an enlarged scale of a venous vascular region proximate the epicardial space depicting the disposition of a guidewire therein;

FIG. 19.2 is a simplified diagrammatic view of the venous vascular region depicted in FIG. 19.1, depicting a pacing lead being advanced into position over the guidewire, thereby dilating small venous structures;

FIG. 19.3 is a simplified diagrammatic view of the venous vascular region depicted in FIG. 19.1, depicting the pacing lead in position after withdrawal of the guidewire, with the body of lead stabilized in the venous circulation.

DETAILED DESCRIPTION OF THE PREFERRED EMBODIMENTS

Figure 1:
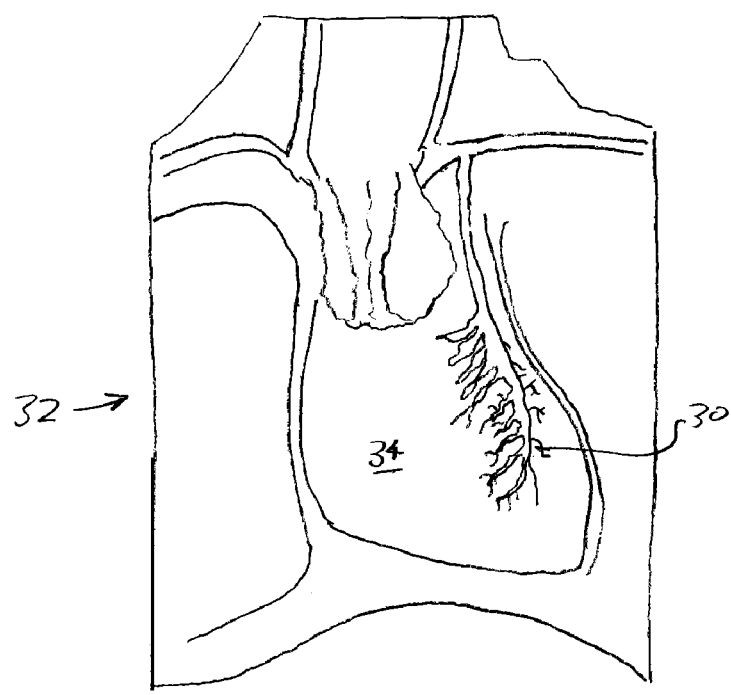
FIG. 1 is a view of the mediastinum opened so as to expose the lungs, pleural space, and the heart enclosed in the pericardial sac.
Figure 2:
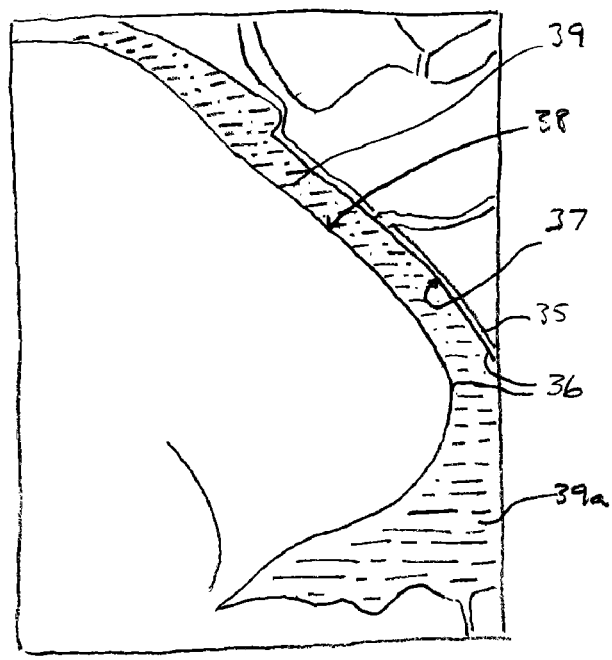
FIG. 2 is a fragmentary cross-sectional view of the heart and pericardium.

Referring to FIGS. 3-6, a pacing lead 40 according to the various embodiments of the present invention generally includes a lead body 41 with a proximal lead portion 42 having a pair of electrodes 44, 46, and presenting a longitudinal lead axis 47, and a resilient fixation portion 48. Resilient fixation portion 48 is preformed in a helical configuration, with the helix being generally symmetrical about a fixation portion axis 50. Fixation portion axis 50 may be generally normal to longitudinal lead axis 47 so that resilient fixation portion 48 extends laterally relative to proximal lead portion 42. Pacing leads are generally known in the art and are disclosed in U.S. Pat. No. 6,321,123 to Morris et al. and U.S. Pat. No. 5,683,445 to Swoyer, both of which are incorporated herein by reference in their entirety.

In the embodiment depicted in FIG. 6, lead body 41 generally includes inner body 52 with defining central lumen 54, inner conductor 56 which is electrically coupled with distal electrode 44, inner insulative sheath 58, outer conductor 60 which is electrically coupled with proximal electrode 46, and outer insulative sheath 62. Electrodes 44, 46, may be structured as rings 64 encircling lead 40, or may be any other structure such as dorsal protuberances 90 (not depicted) enabling electrical coupling with the epicardial wall. Conductors 56, 60, may be coiled wire as commonly used in the art, or may be any other suitable generally flexible conductive structure. Inner body 52 and insulative sheathes 58, 62, may be formed from silicone, polyurethane, or other resilient biocompatible material.

Stylet 66 or a guidewire (not depicted) may be selectively, slidably disposed in central lumen 54 to initially straighten the preformed shape and which then may be withdrawn to enable the preformed shape to develop. Stylet 66 or guidewire (not depicted) enables pacing lead 40 to be selectively maintained in a relatively stiff condition as lead 40 is advanced into and positioned within the venous system and pericardial space. It will be appreciated that in other embodiments of the invention, a guidewire may be employed to initially straighten the lead. In such embodiments, the lead will typically have an end or sidewall aperture proximate the distal end of the lead to enable the lead to be advanced over the guidewire.

As depicted in FIGS. 3-6, resilient fixation portion 48 may be integral with inner body 52 of lead body 41. As previously described, resilient fixation portion 48 may be preformed so as to define a resilient helical structure 68 forming a helical spring extending laterally relative to longitudinal lead axis 47. Helical structure 68 presents a width dimension, annotated "W" in the figures, an uncompressed height dimension annotated "$H_1$" in the figures, and a compressed height dimension annotated "$H_2$" in the figures when disposed in the pericardial space.

Figure 3:
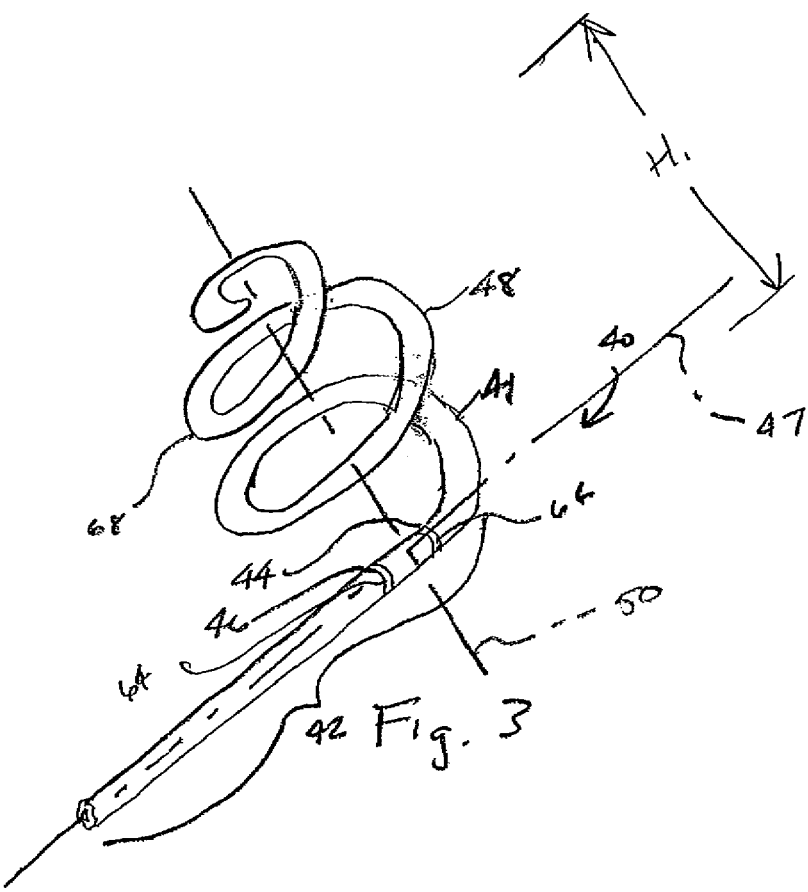
FIG. 3 is a perspective view depicting an embodiment of the pacing lead for the pericardial space according to the present invention.
Figure 4:
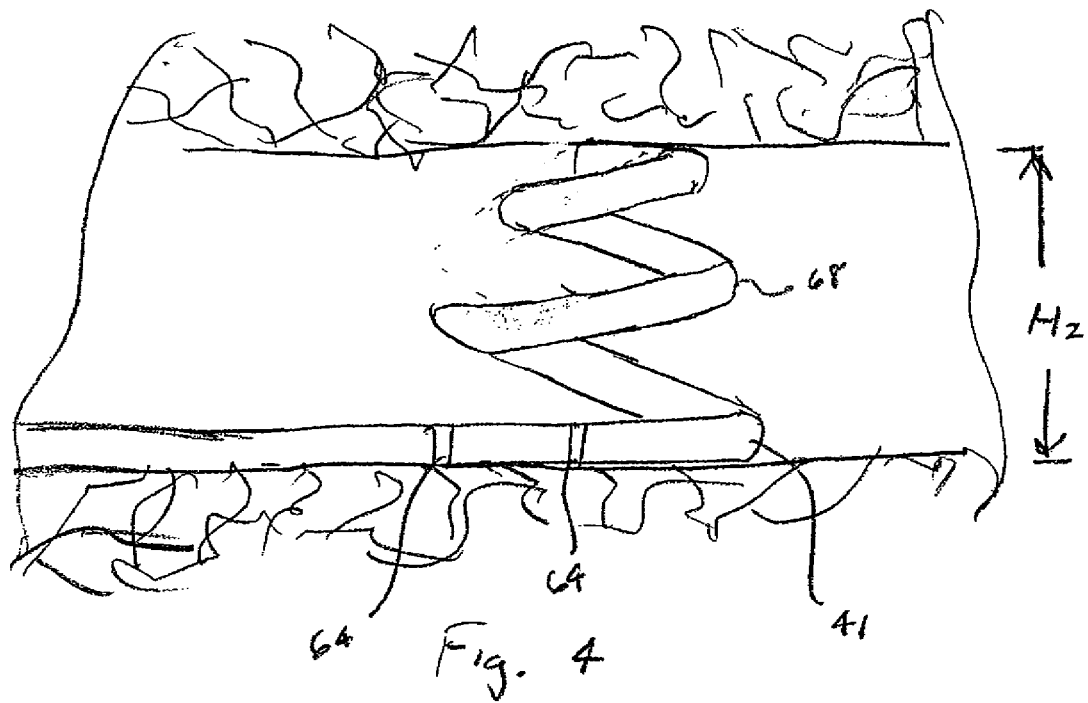
FIG. 4 is a side view of the pacing lead depicted in FIG. 3 deployed in the pericardial space, FIG. 4.1 is a side view of the pacing lead depicted in FIG. 3.1 deployed in the pericardial space.

In alternative embodiments such as depicted in FIGS. 5.1 and 5.2 a lateral s-curve 69 may be provided for additional stability against overturning of fixation portion 48 when implanted within the pericardial space. Moreover, as depicted in FIGS. 3.1, 4.1, and 6.1 a fixation screw element 69.1 or tines 69.2, with or without barbs 69.3 may be employed at the end 69.4 or base 69.5 of fixation portion 48 to provide additional stability.

The biasing force exerted by the resilience of fixation portion 48 is a function of the material properties, the cross-sectional dimension of fixation portion 48, and the amount of lateral deflection, that is, the difference between $H_1$ and $H_2$ of fixation portion 48. The amount of lateral deflection ($H_1-H_2$) of fixation portion 48 will vary depending on the relative resilience of the epicardium and the parietal pericardium, and will generally be between about 0.1 centimeters and 10 centimeters, most typically from about 0.3 centimeters to about 1 centimeter. It will be appreciated that the magnitude of biasing force may be predetermined by adjusting the material properties and dimensions of fixation portion 48 using known principles of engineering. Generally, it is desirable if the compression fixation portion 48 provides between about 1 gram to about 30 grams of biasing force and more desirably between about 3 grams to about 10 grams when emplaced in the pericardial space.

It will be readily appreciated that, in addition to the embodiment discussed above, a pacing lead according to the invention may take a variety of alternative forms, each including a resilient fixation element for biasing one or more electrodes on the lead against the myocardium when the lead is disposed in the pericardial space. For example, in an alternative embodiment depicted in FIGS. 7-9, pacing lead 70 generally includes lead body 72 with proximal lead portion 74 and distal lead portion 76. Proximal lead portion 74 presents longitudinal lead axis 78. Distal lead portion 76 is preformed in a helical configuration, with the helix 80 being generally symmetrical about a fixation portion axis 82 that is generally parallel with longitudinal lead axis 78. Distal lead portion 76 generally includes a first proximal helix 82 a second distal helix 84 and a connecting stabilizing portion 86, which may be formed as an s-shaped curve as depicted, or in any other shape enabling lateral stability against overturning within the pericardial space so as to ensure constant electrical contact for electrodes 90, 92.

Again, lead body 72 defines central lumen 88 for receiving a stylet (not depicted) or guidewire (not depicted) for selectively straightening the lead during implantation. Electrodes 90, 92, may be provided on straight portion 86 or on proximal lead portion 74 (not depicted).

Helix 80 presents a length dimension, annotated "L" in the figures, an uncompressed width dimension annotated "$W_1$" in the figures, and a compressed width dimension annotated "$W_2$" in the figures when disposed in the pericardial space. The biasing force exerted by the helix 80 is a function of the material properties, the cross-sectional dimension of lead body 72, and the amount of deflection, that is, the difference between $W_1$ and $W_2$ of helix 80. The magnitude of biasing force may be predetermined by adjusting the material properties and dimensions of helix 80 using known principles of engineering. Generally, it is desirable if helix 80 provides between about 1 gram to about 30 grams of biasing force and more desirably between about 3 grams to about 10 grams when emplaced in the pericardial space.

In another embodiment depicted in FIGS. 10-12, pacing lead 94 generally includes lead body 96 with proximal lead portion 98 and distal lead portion 100. Proximal lead portion 98 presents longitudinal lead axis 102. Lead body 96 defines central lumen 104 for receiving a stylet (not depicted) for selectively straightening the lead during implantation. Distal lead portion 100 comprises a fixation element 106 having a first portion 108 and a second portion 110, which together define a loop structure 112 laterally adjacent lead portion 98. Including stabilizing extension 113, loop structure 112 presents a width dimension, annotated "$W_3$" in the figures, an uncompressed height dimension annotated "$H_3$" in the figures, and a compressed height dimension annotated "$H_4$" in the figures when disposed in the pericardial space. Either or both of first portion 108 and second portion 110 may be generally arcuate in shape or may be generally straight. In embodiments of the invention, a straight portion 114 may be interposed between first portion 108 and second portion 110. First portion 108 preferably forms an angle γ with longitudinal lead axis 102 of less than 90 degrees. Second portion 110 preferably forms an angle δ with respect to first portion 108 of between about 90 and about 150 degrees. Width dimension $W_3$ is preferably a distance sufficient to inhibit overturning of the lead 94 when emplaced in the pericardial space.

For the purposes of the present invention, the term loop structure includes any lead wherein the lead tip 116, is doubled back along the lead body and a longitudinal axis extending from the lead tip 116 parallels longitudinal lead axis 102 when the tip axis and longitudinal lead axis 102 are projected onto a common plane parallel to and including longitudinal lead axis 102. For instance, the fixation element forming a loop structure may include a plurality of more or less straight segments angled with respect to each other, or a plurality of curved segments of various radii, a single segment with a more or less continuous curve, or a plurality of straight and curved segments joined together. The fixation element and lead body may be made with any material having suitable engineering and biocompatibility properties. The lead electrodes may take any suitable form including without limitation, coils or rings, and "buttons" or protuberances, and may be positioned on the lead body or the fixation element or any combination thereof. It may be relatively more desirable, however, to locate the electrodes proximal to any relatively sharp angles or bends in the lead so as to avoid fractures in the conductors leading to the electrodes.

It will be appreciated that any of the above embodiments may further include such stabilizing and fixation elements as are known in the art such as screw fixation means and tines. The screw fixation means or tines may be located anywhere on the body of the lead or fixation portion as may be desirable so as to promote lead stability when implanted.

It will be further appreciated that biocompatible adhesive may be used as an additional fixation means to ensure stability of the lead. For example, in the embodiment depicted in FIG. 6.2, lead body 41.1 generally includes inner body 52.1 with defining first lumen 54.1, second lumen 54.2, inner conductor 56.1 which is electrically coupled with distal electrode 44.1, inner insulative sheath 58.1, outer conductor 60.1 which is electrically coupled with proximal electrode 46.1, and outer insulative sheath 62.1. Again, electrodes 44.1, 46.1, may be structured as rings 64.1 encircling lead 40.1, or may be any other structure such as dorsal protuberances (not depicted) enabling electrical coupling with the epicardial wall. Conductors 56.1, 60.1, may be coiled wire as commonly used in the art, or may be any other suitable generally flexible conductive structure. Inner body 52.1 and insulative sheathes 58.1, 62.1, may be formed from silicone, polyurethane, or other resilient biocompatible material.

First lumen 54.1 has open end 54.3 to enable guidewire 66.1 to pass through so that lead 40.1 may be advanced into position over guidewire 66.1. Guidewire 66.1 may be selectively, slidably disposed in first lumen 54.1 to initially straighten the preformed shape and which then may be withdrawn to enable the preformed shape to develop.

Second lumen 54.2 may have end opening 54.4 or one or more sidewall openings 54.5 or any combination thereof. Openings 54.4, 54.5, are positioned wherever application of adhesive for fixation of lead 40.1 is desired, for example at lead end 54.6, proximate fixation portion base 69.5, or proximate electrodes 44.1, 46.1.

When lead 40.1 is positioned on the epicardium, adhesive in the form of biocompatible glue such as for example cyanoacrylate (butyl-2-cyanoacrylate monomer), Dermabond (2-octyl cyanoacrylate), Fibrin, or BioGlue (biological bovine serum albumin and glutaraldehyde), may be forced through second lumen 54.2. The glue will exit lumen openings 54.4, 54.5 and be F deposited in the desired location in order to cement lead 40.1 in place.

In addition to embodiments wherein liquid adhesive is applied through openings from a lumen in the lead, it will also be appreciated that in other embodiments, a solid adhesive may be disposed at predetermined locations on the lead. In such embodiments, the solid adhesive is activated by blood or other fluid when the lead is emplaced.

Moreover, as depicted in FIGS. 6.3 and 6.4, the efficacy of the adhesive bond may be enhanced with a patch or band of absorbant material 54.7 disposed over the lumen openings 54.4, 54.5. Absorbant material 54.7 may be any suitably biocompatible material, such as polytetrafluoroethylene (PTFE) felt, that will "wick" adhesive from lumen openings 54.4, 54.5. It will be appreciated that the wicking action may be enhanced by selecting an adhesive 54.8 having a relatively low viscosity, such as Dermabond. Absorbent material 54.7 may be attached to lead 40.1 on outer surface 40.2 or may be insert molded in lead body 41.1 so that outer surface 54.81 of absorbent material 54.7 is flush with outer surface 40.2.

In operation, with lead 40.1 positioned as desired in pericardial space 39, adhesive 54.8 is introduced proximate lumen openings 54.4, 54.5, through second lumen 54.2 Adhesive 54.8 may be forced directly through the length of second lumen 54.2 as depicted in FIG. 6.3, or may be introduced only in the vicinity of lumen openings 54.4, 54.5, using a hollow stylet 66.2 as depicted in FIG. 6.5. Adhesive 54.8 is drawn into and through absorbent material 54.7 by capillary action. When adhesive 54.8 sets, absorbent material 54.7 and lead body 41.1 are adhered to the tissue with which they are in contact.

In an embodiment depicted in FIGS. 5.3-5.7 and 6.5, lead 40.11 generally includes lead body 41.11 with inner body portion 52.11 defining lumen 54.11, which may have either a closed end 54.31 or an open end (not depicted) to accommodate a guide wire (not depicted) to enable emplacement of the lead as previously described. A first electrode 44.11 is provided on lead body 41.11 proximate base 69.51 of fixation portion 48.11, while a second electrode 46.11 is disposed proximate end 54.31. Fixation portion 48.11 may be formed as a generally symmetrical helix with a single rotation. Preferably, fixation portion 48.11 may have an uncompressed height $H_{11}$ of from about 0.2 cm to about 4 cm.

The spaced apart disposition of electrodes 44.11, 46.11, proximate base 69.51 and end 54.31, respectively, enables fixation portion 48.11 to be positioned in either a first "upright" orientation as depicted in FIG. 5.6, wherein electrode 44.11 is contacting visceral pericardium 38 while electrode 46.11 is contacting parietal pericardium 37, or in a second "inverted" position as depicted in FIG. 5.7, wherein electrode 46.11 is contacting visceral pericardium 38 while electrode 44.11 is contacting parietal pericardium 37. As a consequence, even if lead 40.11 "flips-over" so as to become inverted within pericardial space 39, electrodes 44.11, 46.11, will maintain electrical contact so that pacing is not interrupted.

As before, lumen 54.11 may have one or more adhesive openings 54.4, 54.5, to enable application of adhesive for fixation of lead 40.11. Openings 54.4, 54.5, are positioned wherever application of adhesive for fixation of lead 40.11 is desired, for example at lead end 54.31, proximate fixation portion base 69.51, or proximate electrodes 44.11, 46.11. Absorbent material 54.7 may be disposed proximate and/or over openings 54.4, 54.5, to facilitate distribution of adhesive 54.8 and to improve the resultant tissue bond. Again, the adhesive 54.8 may be forced directly through lumen 54.11, or may be applied only in the vicinity of openings 54.4, 54.5, though lumen 66.3 of hollow stylet 66.2.

It will be readily appreciated that adhesive fixation means in accord with the present invention may be incorporated as desired to provide stability to any pericardial lead by enabling cementation of the lead at desired locations, especially proximate electrodes. Moreover, with the compression fixation elements of any of leads 40, 40.1, 40.11, 74, 94, the electrodes may be disposed spaced apart so as to engage both the visceral pericardium 38 and parietal pericardium 37 when disposed in pericardial space 39 to alleviate lack of electrical contact due to overturning of the lead.

For example, referring to FIGS. 6.6-6.9, a pacing lead 340 generally includes a lead body 341 with a proximal lead portion 342 having a pair of electrodes 344, 346, and presenting a longitudinal lead axis 347, and a resilient compression fixation portion 348. Resilient compression fixation portion 348 is preformed in a generally helical configuration having a single coil 349, with coil 349 being generally symmetrical about a fixation portion axis 350. Fixation portion axis 350 may be generally normal to longitudinal lead axis 347 so that resilient fixation portion 348 extends laterally relative to proximal lead portion 342. Coil 349 presents a width dimension, annotated "$W_{10}$" in the figures, and an uncompressed height dimension annotated "$H_{11}$" in the figures.

The biasing force exerted by the resilience of coil 349 is a function of the material properties, the cross-sectional dimension of coil 349, and the amount of lateral deflection, that is, the difference between $H_{11}$ and the compressed height of coil 349 when emplaced in pericardial space 39. The amount of deflection of coil 349 will vary depending on the relative resilience of the epicardium and the parietal pericardium, and will generally be between about 0.1 centimeters and 10 centimeters, most typically from about 0.3 centimeters to about 1 centimeter. It will be appreciated that the magnitude of biasing force may be predetermined by adjusting the material properties and dimensions of coil 349 using known principles of engineering. Generally, it is desirable if coil 349 provides between about 1 gram to about 30 grams of biasing force and more desirably between about 3 grams to about 10 grams when emplaced in pericardial space 39.

Lead body 341 generally includes inner body 352 defining lumen 354, inner conductor 356 which is electrically coupled with distal electrode 344, inner insulative sheath 358, outer conductor 360 which is electrically coupled with proximal electrode 346, and outer insulative sheath 362. Stylet 366 or a guidewire (not depicted) may be selectively, slidably disposed in lumen 354 to initially straighten the preformed shape and which then may be withdrawn to enable the preformed shape to develop. As depicted, stylet 366 may be hollow, defining lumen 366.1 to enable introduction of adhesive as described further hereinbelow. Although electrodes 344, 346, are both depicted on the same side of coil 349, it will be appreciated that, in an alternative embodiment, one of electrodes 344, 346, may be disposed on the other side of coil 349 to enable the lead to be oriented in either an upright or inverted position as previously described.

Adhesive openings 368, 370, 372, 374, 376, may be provided, extending from lumen 354 to exterior surface 378 of lead 340 to enable application of adhesive for fixation of lead 340. Openings 368, 370, 372, 374, 376, are positioned wherever application of adhesive for fixation of lead 340 is desired, for example at lead end 353, on top surface 380 of coil 349, or proximate electrodes 344, 346. Again, absorbent or other material 382 exhibiting capillary action may be disposed proximate and/or over the adhesive openings, to facilitate distribution of adhesive and to improve the resultant tissue bond. As depicted in FIGS. 6.6-6.9, a ring of material 382 is disposed around openings 368, 370, and 372, while a band of material 382 is disposed around lead 340 covering openings 374, 376. Again, the adhesive may be forced directly through lumen 354, or may be applied only in the vicinity of openings 368, 370, 372, 374, 376, though lumen 366.1 of hollow stylet 366.

Leads 40, 40.1, 40.11, 74, 94, 340, may be disposed in pericardial space 39 by any suitable method either surgically or percutaneously. In an exemplary embodiment, pacemaker lead 40, 40.1, 40.11, 74, 94, 340, is disposed in pericardial space 39, on or in the epicardium or in the microvasculature by first disposing an elongate instrument into the venous system of the heart and puncturing the venous system at a predetermined position, disposing the elongate instrument into the pericardial space, epicardium or in the microvasculature at a predetermined location in the pericardial space, epicardium or in the microvasculature; and disposing a pacemaker lead at the predetermined position. It should be clear that lead 40, 40.1, 40.11, 74, 94, 340, can be disposed either into the pericardial space 39 or into the vascular mesh in or on the heart wall surface just adjacent to pericardial space 39. Other suitable methods for introduction of the lead 40, 40.1, 40.11, 74, 94, 340, of the present invention into the pericardial space or the microcirculation are disclosed in published U.S. patent application Ser. No. 10/497,763, entitled METHOD AND APPARATUS FOR ANCHORING OF PACING LEADS, hereby fully incorporated herein by reference.

Figure 13:
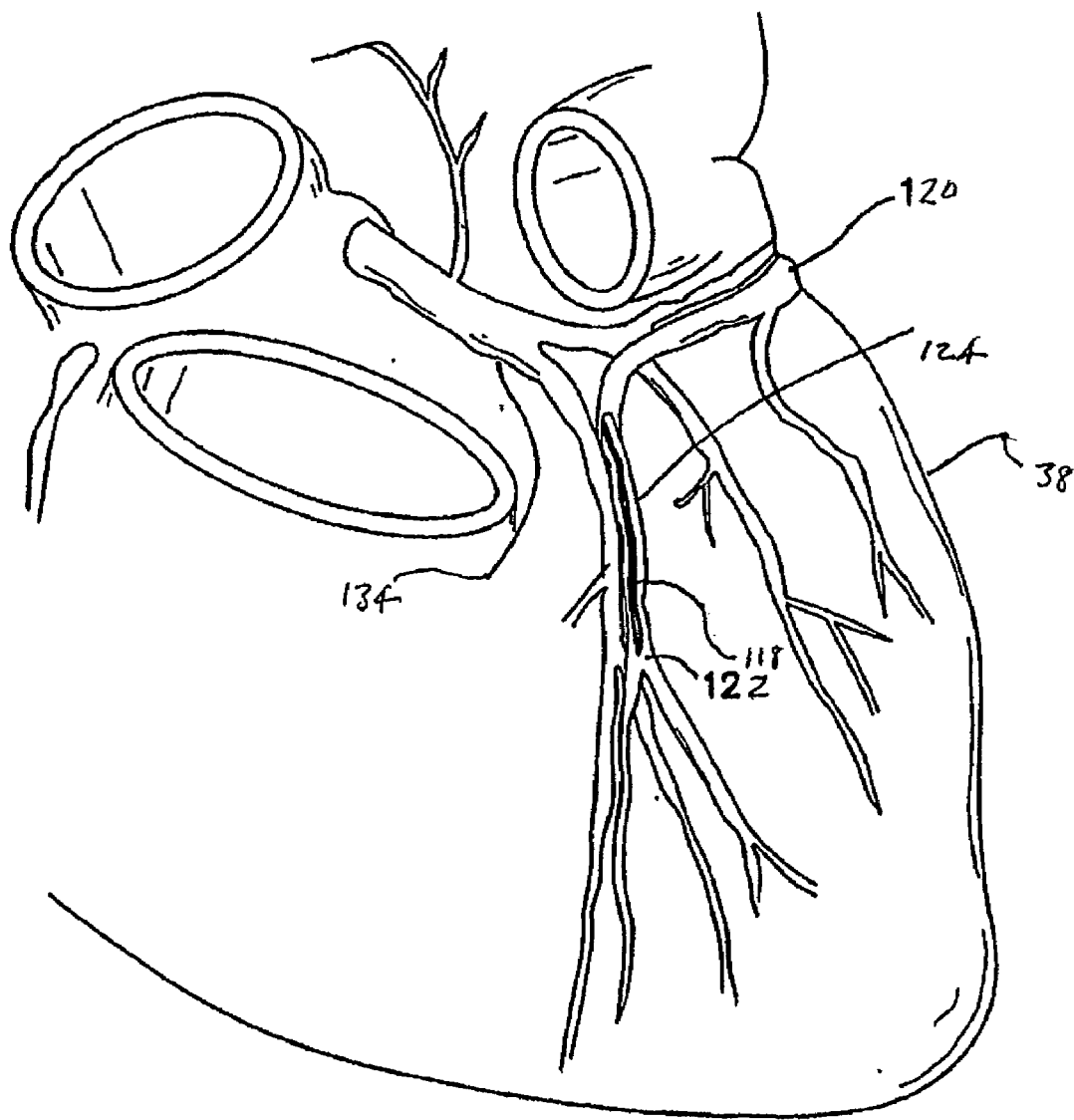
FIG. 13 is a simplified diagrammatic, partially cut-away side view of a human heart depicting the vascular system of the heart.

The step of disposing a pacemaker lead at the predetermined position includes disposing the lead in a position on the surface of the left ventricle in a position of optimized pacing efficacy through the venous microvasculature on the ventricular surface or in the pericardial space. In an embodiment the elongate instrument may be disposed into a first venous bed through the vascular mesh and subsequently into a second venous drainage bed for optimal positioning at or near the ventricular surface or adjacent pericardial space. The microvasculature may also be dilated prior to implanting the pacemaker lead in order to allow for access of the guiding instrument or lead. In either case, the biasing force exerted by the resilient fixation element of the pacemaker lead 40, 40.1, 40.11, 74, 94, 340, in combination with friction, and adhesive in some embodiments, is used to fix the lead in place and bias the lead electrodes against the epicardium for good electrical conductivity. Returning to the exemplary embodiment of a method according to an embodiment of the invention, and referring now to FIGS. 13-20, a wire, catheter, lead, introducer or other instrument 118 is endovascularly disposed by conventional means into the coronary venous system 120 to a point 122 in the coronary venous system 120 where a puncture of the venous system 120 may take place as depicted in FIG. 13.

At this point 120, a coronary vein 124 is punctured or otherwise opened to allow the disposition of the wire, catheter, lead, introducer or other instrument 118 to be disposed through the vein 124 and then inserted, steered or disposed in the pericardial space 39 to the desired location on the myocardial surface.

Figure 14:
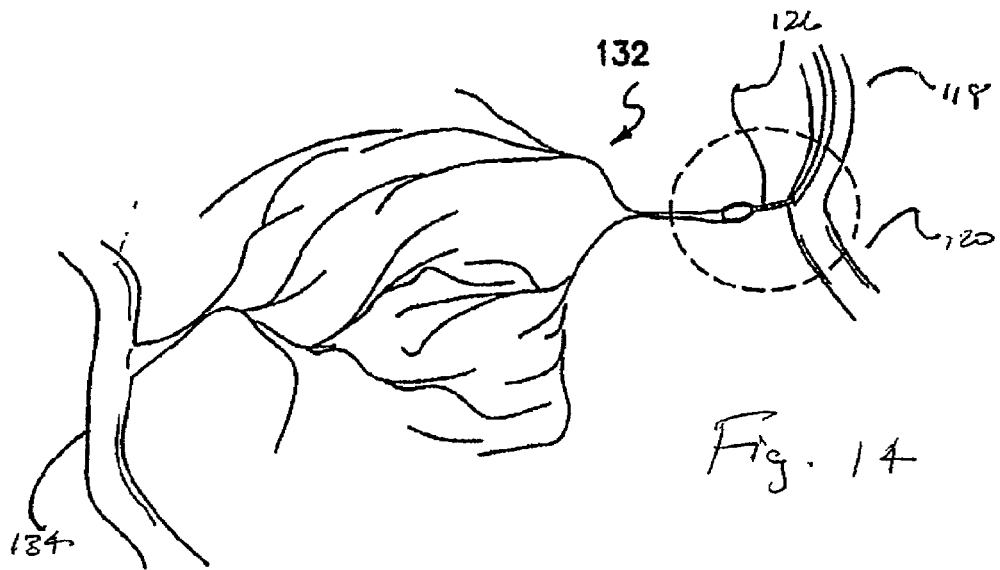
FIG. 14 is a simplified diagram of the venous vascular mesh on the epicardial surface.
Figure 15:
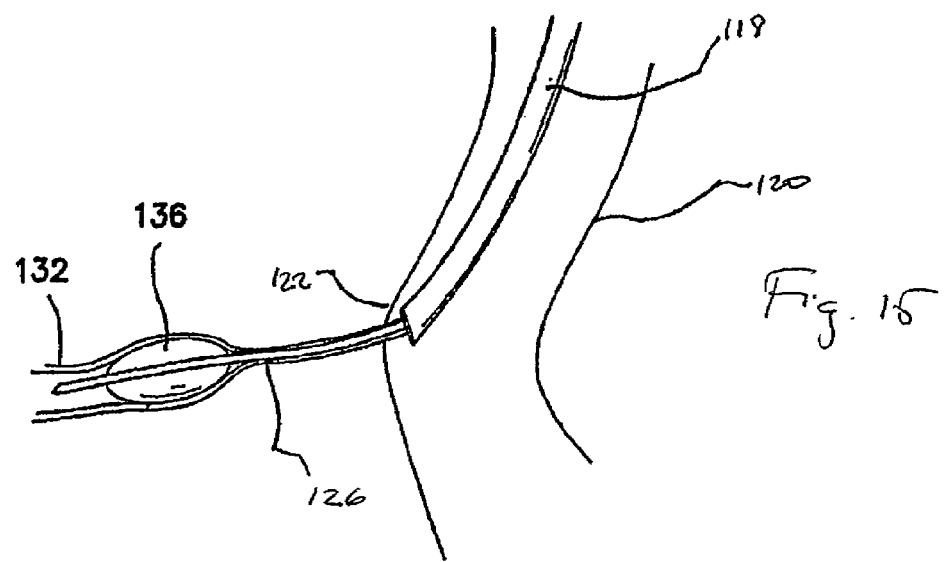
FIG. 15 is a simplified diagrammatic side cross section view of an enlarged scale of the region in circular dotted outline in FIG. 14 depicting dilation of the microvasculature with a balloon prior to insertion of a pacing lead.
Figure 16:
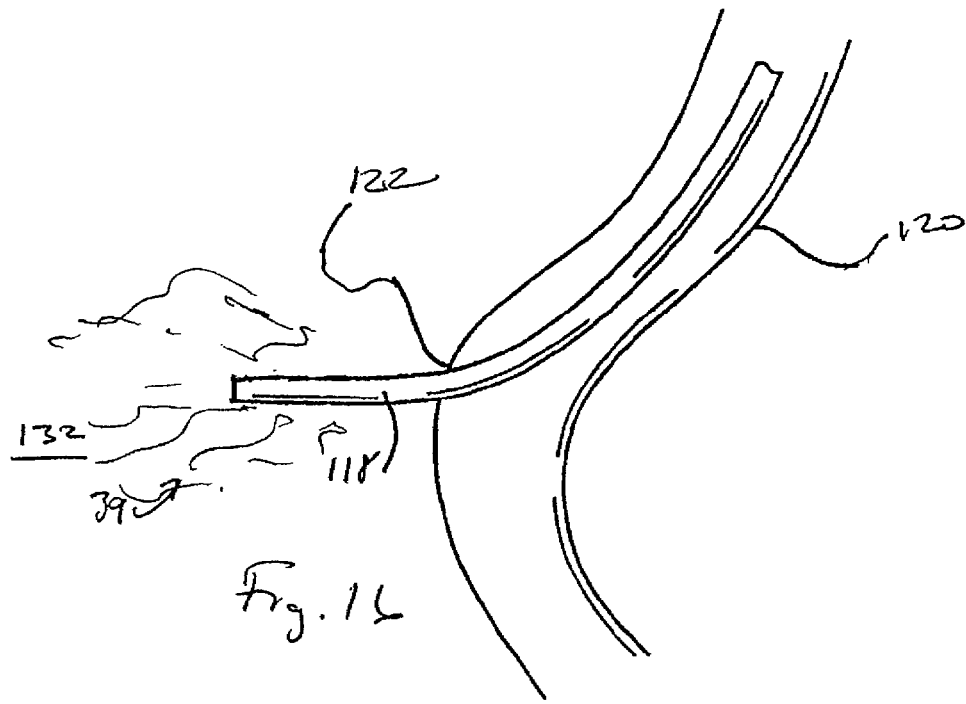
FIG. 16 is a simplified diagrammatic side cross section view of the region of FIG. 15 depicting the disposition of a catheter into the microvasculature or pericardial space.

There are many means whereby the incision or puncture through the wall of vein 124 may be accomplished. A hollow or solid needle 126 as depicted in FIGS. 14 and 15 can be disposed through a catheter 118 and positioned at the venous site 122 selected. Advancement of the needle 126 beyond the distal tip of the catheter 118 enables the needle to puncture the vein 124 at the desired location 122. The vein 124 may also be punctured employing cutting or puncturing probes using ohmic heating, laser light, radiofrequency or microwave heating, ultrasonic or other energy sources, a balloon or blunt probe may also be used to open the vein into the pericardial space.

Once the vein 124 is punctured confirmation must be obtained that entry into the pericardial space 39 is accomplished. This can be practiced by injecting a contrast agent through the puncture site 122 into the pericardial space 39, obtaining an ultrasound image of the field of operation, or inserting a guidewire or other radio opaque means into the puncture site 122 for fluoroscopic confirmation.

Figure 17:
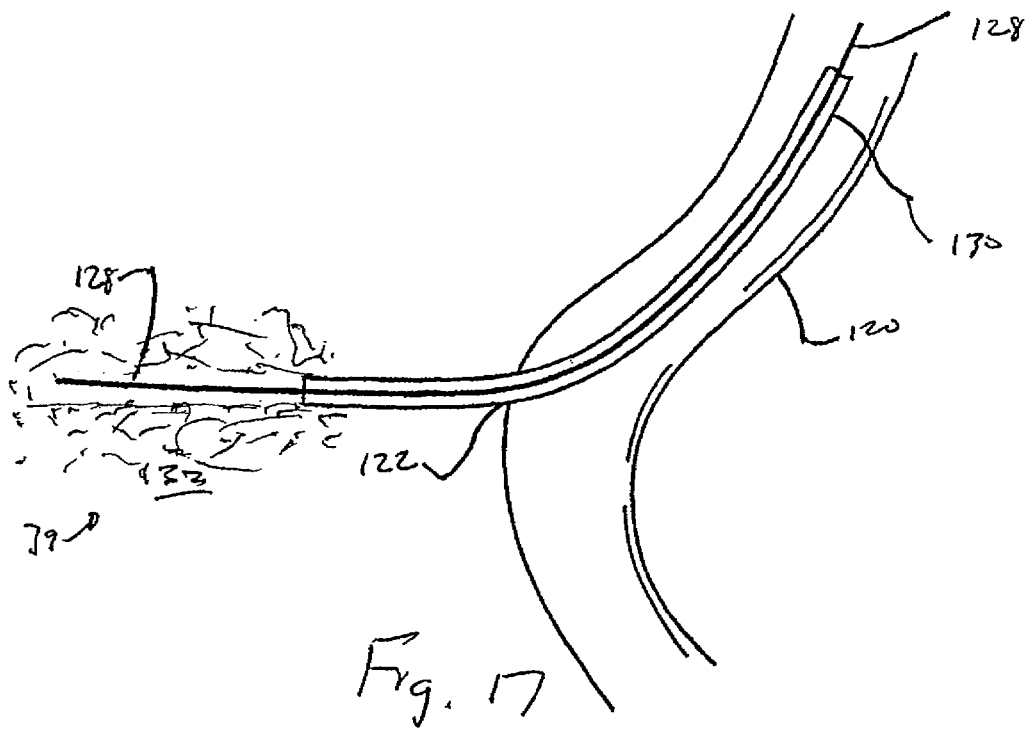
FIG. 17 is a simplified diagrammatic side cross section view of the region of FIG. 15 depicting the disposition of a guidewire and introducer into the microvasculature or pericardial space.

With confirmation of entry into the pericardial space 39 a guidewire or probe 128 is then advanced into the space 39 through catheter 118, which may be removed and then followed, if desired, by an introducer or other introducing instrument 130 which is steerable or otherwise navigable to the desired location in the pericardial space 39 adjacent to or proximal to the desired location in the left ventricular wall as shown in FIG. 17.

Figure 18:
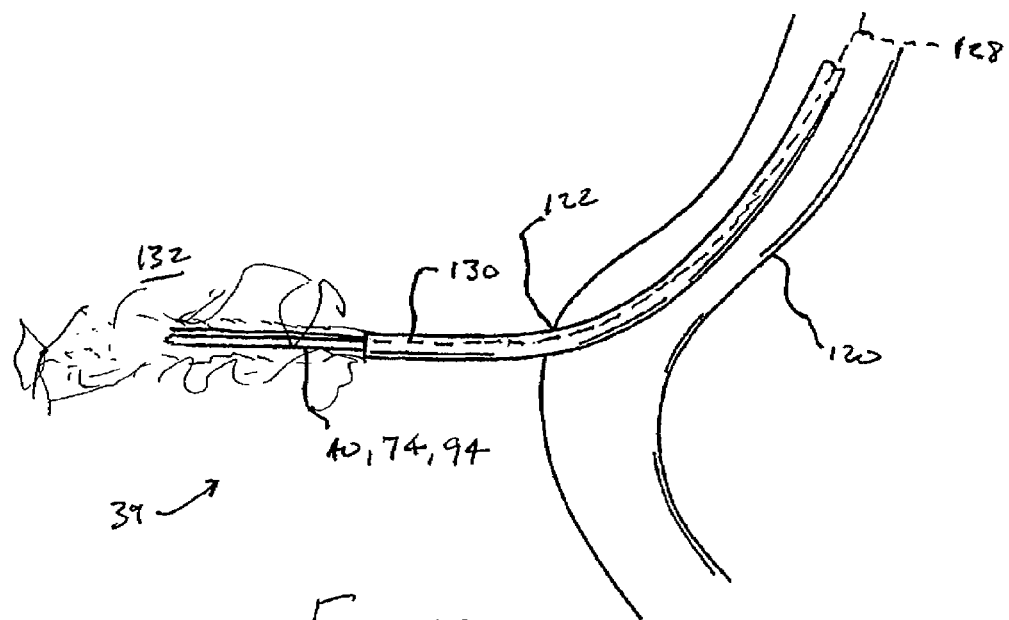
FIG. 18 is a simplified diagrammatic side cross section view of the region of FIG. 15 depicting the disposition of a pacemaker lead into the microvasculature or pericardial space.
Figure 20:
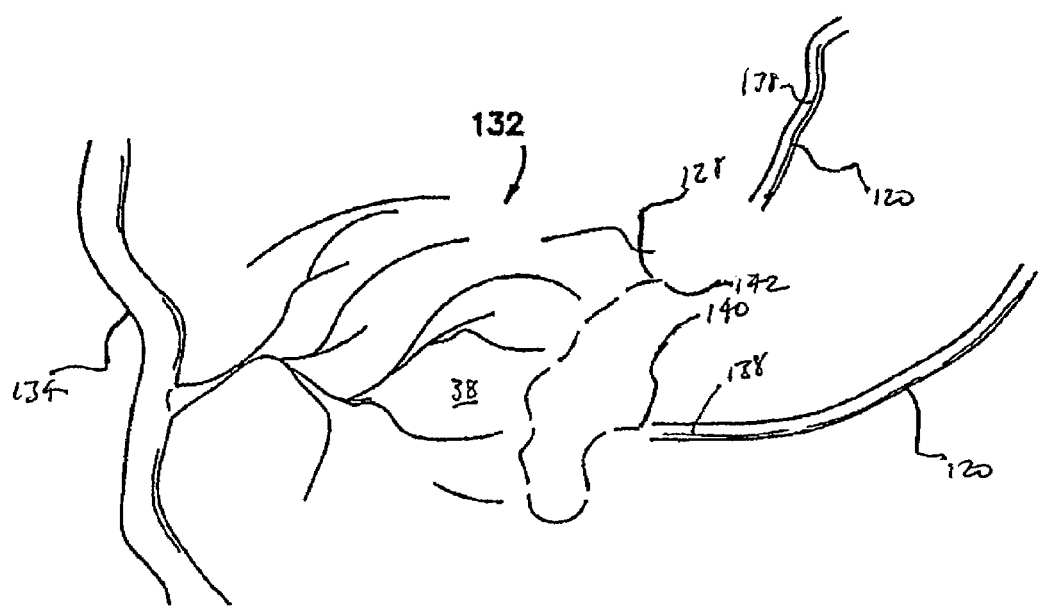
FIG. 20 is a simplified diagrammatic side view of the disposition of an elongate instrument from a first venous bed through the venous vascular mesh and implantation in a second venous drainage area to enable emplacement of a pacing lead.

Finally, a pacing lead 40, 40.1, 40.11, 74, 94, 340, straightened with stylet 66 is then brought or disposed at the desired location using the introducer or other introducing instrument 130 or the pacing lead 40, 40.1, 40.11, 74, 94, 340, itself may be self-guiding as depicted in FIG. 18. Once the desired location has been accessed; the stylet 66 is withdrawn from the lead 40, 40.1, 40.11, 74, 94, 340, enabling it to assume its preformed shape, compressed between the parietal paricardium and epicardium as depicted in FIG. 19, keeping the electrodes oriented toward the myocardium. In the case of patients who have cardiac bypass surgery, the pericardial space 39 often includes adhesive tissues, which provide a naturally adhesive or embedding tissue field, enhancing frictional engagement of the lead.

It will be appreciated by those of skill in the art that when lead 40, 40.1, 40.11, 74, 94, 340, is introduced transvenously into the heart and from there into the pericardial space through the coronary venous structure, the proximal portion of lead 40, 40.1, 40.11, 74, 94, 340, will be stabilized and supported within the venous system. Moreover, by using the coronary venous microcirculation as a means to access the pericardial space, the final position of the lead and the site where the lead exits the vein into the pericardial space can be kept in close proximity. By comparison, standard leads that stay within the vein can only be placed where there are veins large enough to accommodate the body of the lead. With a lead and method according to the invention, small veins may be used to position the guide wire where the lead is to be positioned, and the lead may then be advanced along the wire to the desired site by dilating the small veins to the point of rupture at which point the tip of the lead is not within the vein and the tip may be stabilized to ensure electrode contact.

For example, as depicted in FIGS. 19.1-19.3, guidewire 200 may be advanced through large 202 and small 204 coronary veins into desired lead implantation region 206 which may be within the pericardial space. Next, lead 40, 40.1, 40.11, 74, 94, 340, is advanced over guidewire 200, dilating small veins 204 to the point of rupture as depicted in FIG. 19.2. Once lead 40, 40.1, 40.11, 74, 94, 340, is properly positioned, guidewire 200 is withdrawn to enable 40, 40.1, 40.11, 74, 94, 340, to assume its pre-formed shape as depicted in FIG. 19.3. The proximal portion 208 of lead 40, 40.1, 40.11, 74, 94, 340, is stabilized by virtue of close frictional engagement within small veins 204, while lead tip 210 is stabilized by fixation portion 48.

No restrictions or limitations are envisioned as being included which would in any way reduce the scope of the means whereby the wire, catheter, lead or other instrument 118, 128, 130, or 40, 40.1, 40.11, 74, 94, 340, may be steered, by which the vein 124 is punctured, by which the vein is sealed around the wire, catheter, lead, other instrument, 118, 128, 130, or pacing lead 40, 40.1, 40.11, 74, 94, 340, or by which the lead 40, 40.1, 40.11, 74, 94, 340, is secured at the desired location.

Lead, 40, 40.1, 40.11, 74, 94, 340, may also be disposed in the vascular mesh. The ventricular surface of the heart has disposed therein and/or thereon a microvasculature 132 as diagrammatically shown in FIG. 14 between the arterial system 134 and venous system 120 forming what comprises a vascular mesh. The vascular mesh is comprised of a multiplicity of small vessels radiating from the more distal portions of the coronary venous system. The vascular mesh subdivides into smaller and smaller multi-branched vessels and ultimately communicates to the capillary system in the heart walls. Blood drains from the heart muscle into the vascular mesh and then into the coronary veins. Generally, a flow path can be found through the vascular mesh communicating one vessel of the coronary venous system with another vessel of the coronary venous system.

The microvasculature 132 may also be opened or dilated with a balloon 136 or blunt instrument that opens the distal microvasculature 132 to allow for a catheter or other instrument 118 to be advanced. The balloon 136 may be withdrawn, or a central channel through a balloon catheter 118 may be used to withdraw needle 126, so that another catheter, lead or other instrument 118 can be deployed into the microvasculature 132.

In one embodiment access to the venous system 120 through the coronary sinus is accomplished using a fine, flexible 0.014 inch guidewire 138. The guidewire 138 is steered through a selected venous path to the very end of a venous bed 140 shown in, FIG. 19. At the end of a venous bed 140, the vascular system 120, 134, communicates with an adjacent vascular bed through a vascular mesh 132 located on the epicardium 38 and also communicating with one or more other venous beds 142. Theoretically, a path can be traced through the vascular mesh 132 between any two venous beds 140 and 142 in the entire cardiac vascular system 120, 134. In theory the wire 138 can be advanced through the vascular mesh 132 into an adjacent or another venous bed 140 and ultimately looping back to the coronary sinus.

In this manner the wire 138 can be then steered from a first venous bed 140 to a selected position in a second venous bed 142, which position 140 might be accessible or easily accessible through the coronary sinus and the second venous bed 142 accessible as a practical matter only by a path through the coronary sinus, the first venous bed 140, the vascular mesh 132 and into the second venous bed 142. Therefore, the ideal or desired position for a pacing lead becomes accessible even if located in the second venous bed 142 through the first venous bed 140.

The pacemaker lead 142 is stabilized in its position by virtue of its frictional engagement or intimacy with the terminal end of the first venous bed 140 and with the vascular mesh 132. If necessary, the end of the first venous bed 140 and the vascular mesh 132 can be opened by positioning an angioplasty balloon 136 on the guidewire 138 at the position of terminal constriction of the first and second venous beds 140, 142 and in the vascular mesh 132. This allows for the easy passage then of a pacemaker lead 40, 40.1, 40.11, 74, 94, 340, through the terminal constriction of the first and second venous beds 140, 142, and the vascular mesh 132. The lead 40, 40.1, 40.11, 74, 94, is then secured in position in the second venous bed 142 by virtue of its embedment in the terminal constriction of the first and second venous beds 140, 142, and/or the vascular mesh 132.

It is further possible that use of the balloon 136 may be used to intentionally rupture the microvasculature 132 allowing the lead 40, 40.1, 40.11, 74, 94, 340, to then enter the pericardial space 39 and become anchored therein as described above in a manner similar to venous puncture.

Although the present invention has been described with reference to particular embodiments, one skilled in the art will recognize that changes may be made in form and detail without departing from the spirit and the scope of the invention. Therefore, the illustrated embodiments should be considered in all respects as illustrative and not restrictive.

What is claimed is:

1. A pacing lead for implantation in a pericardial space defined between an epicardial wall and a parietal pericardial wall, the epicardial wall and the parietal pericardial wall defining a height dimension of the pericardial space, the pacing lead comprising:
   an elongated lead body presenting a longitudinal axis;
   a generally helically shaped resilient fixation element extending from the elongated lead body along an axis oriented in a direction generally normal to the longitudinal axis, the resilient fixation element presenting a predetermined height dimension greater than the height dimension of the pericardial space, the lead body and the resilient fixation element defining a first lumen for receiving a stylet or guidewire such that the stylet or guidewire is selectively slidable in the first lumen to temporarily straighten the resilientfixation element to thereby facilitate implantation of the pacing lead in the pericardial space; and
   at least one electrode on either the lead body or the resilient fixation element, wherein when the resilient fixation element is emplaced within the pericardial space, the resilient fixation element is compressed between the epicardial wall and the parietal pericardial wall and thereby exerts a biasing force, biasing the at least one electrode against the epicardial wall.

2. The lead of claim 1, wherein the lead includes a pair of electrodes.

3. The lead of claim 1, wherein the lead defines an aperture extending from the first lumen to an exterior surface of the lead.

4. The lead of claim 1, further comprising a stylet or guidewire.

5. The lead of claim 1, wherein the lead body defines a second lumen for transporting adhesive for fixing the lead.

6. The lead of claim 5, wherein the biasing force exerted by the resilient fixation element is between about 3 grams and about 10 grams.

7. The lead of claim 1, wherein the biasing force exerted by the resilient fixation element is between about 1 gram and about 30 grams.

8. The lead of claim 1, further comprising a fixation screw element or fixation tines.

9. The lead of claim 1, further comprising a fixation screw element or fixation tines. pericardial wall.

10. A pacing lead for implantation in a pericardial space defined between an epicardial wall and a parietal pericardial wall, the epicardial wall and the parietal pericardial wall defining a height dimension of the pericardial space, the pacing lead comprising:
   an elongated lead body presenting a longitudinal axis;
   a resilient compression fixation element extending from the elongated lead body about an axis oriented in a direction generally normal to the longitudinal axis, the resilient compression fixation element presenting a predetermined height dimension greater than the height dimension of the pericardial space, the lead body and the resilient fixation element defining a first lumen for receiving a stylet or guidewire such that the stylet or guidewire is selectively slidable in the first lumen to temporarily straighten the resilient fixation element to thereby facilitate implantation of the pacing lead in the pericardial space; and
   a first electrode on one of the lead body or the resilient fixation element, wherein when the resilient fixation element is emplaced within the pericardial space, the resilient fixation element is compressed between the epicardial wall and the parietal pericardial wall and thereby exerts a biasing force, biasing the first electrode against the epicardial wall.

11. The lead of claim 10, wherein the lead further comprises a second electrode, the second electrode spaced apart from the first electrode and disposed on the other of the lead body or the resilient fixation element, wherein when the resilient fixation element is emplaced within the pericardial space, the first electrode is biased against the epicardial wall while the second electrode is biased against the parietal pericardial wall.

12. The lead of claim 10, wherein the lead defines at least one aperture extending from the first lumen to an exterior surface of the lead.

13. The lead of claim 12, wherein the lead further includes absorbent material for distributing adhesive disposed proximate the at least one aperture.

14. The lead of claim 13, wherein the absorbent material covers the at least one aperture.

15. The lead of claim 12, wherein the lead includes a plurality of apertures extending from the first lumen to the exterior of the lead.

16. The lead of claim 15, wherein the lead includes a plurality of electrodes and wherein each of the plurality of apertures is disposed proximate one of the plurality of electrodes.

17. The lead of claim 10, wherein the lead body defines a second lumen for transporting adhesive for fixing the lead.

* * * * *

UNITED STATES PATENT AND TRADEMARK OFFICE
CERTIFICATE OF CORRECTION

PATENT NO. : 8,036,757 B2  Page 1 of 1
APPLICATION NO. : 11/535374
DATED : October 11, 2011
INVENTOR(S) : Seth Worley It is certified that error appears in the above-identified patent and that said Letters Patent is hereby corrected as shown below:

Column 14, Claim 1, line 14, please delete "resilientfixation" and insert --resilient fixation--;
Column 14, Claim 9, line 42, please delete "pericardial wall."

Signed and Sealed this
Twenty-sixth Day of June, 2012

David J. Kappos
*Director of the United States Patent and Trademark Office*